United States Patent
Feron et al.

(10) Patent No.: US 12,076,352 B2
(45) Date of Patent: Sep. 3, 2024

(54) IMMUNOGENIC COMPOSITION

(71) Applicant: GLAXOSMITHKLINE BIOLOGICALS SA, Rixensart (BE)

(72) Inventors: Christiane Marie-Paule Simone Jeanne Feron, Rixensart (BE); Sandra Giannini, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 820 days.

(21) Appl. No.: 16/973,471

(22) PCT Filed: Jun. 18, 2019

(86) PCT No.: PCT/EP2019/065974
§ 371 (c)(1),
(2) Date: Dec. 9, 2020

(87) PCT Pub. No.: WO2019/243307
PCT Pub. Date: Dec. 26, 2019

(65) Prior Publication Data
US 2021/0252081 A1    Aug. 19, 2021

Related U.S. Application Data

(60) Provisional application No. 62/686,889, filed on Jun. 19, 2018.

(51) Int. Cl.
*A61K 35/76*        (2015.01)
*C12N 7/00*         (2006.01)

(52) U.S. Cl.
CPC ............... *A61K 35/76* (2013.01); *C12N 7/00* (2013.01); *C12N 2795/00043* (2013.01); *C12N 2820/55* (2013.01)

(58) Field of Classification Search
None
See application file for complete search history.

(56) References Cited

FOREIGN PATENT DOCUMENTS

| WO | WO 2012/163810 A1 | 12/2012 |
| WO | WO 2017/114979 A1 | 7/2017 |

OTHER PUBLICATIONS

Hatfull and Hendrix, Curr. Opin. Virol., Oct. 2011, 1(4):298-303. (Year: 2011).*
Hajam et al., "Bacterial flagellin—a potent immunomodulatory agent," Experimental & Molecular Medicine (2017), vol. 49, e373, pp. 1-15.
Leroux-Roels et al., "Phase I, randomized, observer-blind, placebo-controlled studies to evaluate the safety, reactogenicity and immunogenicity of an investigational non-typeable *Haemophilus influenzae* (NTHi) protein vaccine in adults," Vaccine (2016) vol. 34, pp. 3156-3163.
Nobrega et al., "Revisiting phage therapy: new applications for old resources," Trends in Microbiology (Apr. 2015), vol. 23, No. 4, pp. 185-191.

* cited by examiner

*Primary Examiner* — Stacy B Chen
(74) *Attorney, Agent, or Firm* — Birch, Stewart, Kolasch & Birch, LLP

(57) ABSTRACT

The present invention discloses an engineered bacteriophage capable of binding to a commensal bacterium and inserting its genome polynucleotide into the commensal bacterium, but incapable of producing progeny, incapable of carrying out a lysogenic cycle and incapable of carrying out a lytic cycle within the commensal bacterium, wherein the engineered bacteriophage comprises a genome polynucleotide including at least one gene encoding at least one heterologous antigen(s) under the control of a promoter.

17 Claims, 12 Drawing Sheets
Specification includes a Sequence Listing.

Minimum synthetic phage genome: incapable of lysogeny or propagation, only genome amplification

Expression of bio-film destroying enzyme.

Modified tail fibers/plate: broaden strain recognition.

Engineered phage genome Containing at least one antigen gene with a suitable promoter Overexpression of heterologous cargo (ie antigen)

Post III

20100673 : Mice immunization with C. difficile ToxA-Cter, ToxB-Cter and fusion proteins 2d generation formulated in AS03B
Inhibition hemagglutination assay : mid-point titers on Post III sera

| Antigen | 10µg Ag/dose | 3µg Ag/dose |
|---|---|---|
| ToxA (aa 2387-2706) | 1280 | 1280 |
| ToxB (aa 1750-2360) | 60 | 240 |
| F1 | 5120 | 7680 |
| F2 | 3840 | 3840 |
| F3 | 1920 | 1920 |
| F4 | 1920 | 1920 |
| F5 | 5120 | 3840 |
| AS03B adjuvant only | | 40 |

PE-WT sequence
MKKIILTLSLGLLLTACSAQIQKAKQNDVKLAPPTDVRSGYIRLVKNVNYYIDSESIWVDNQEPQIVHFDAVVNLD
KGLYVYPEPKRYARSVRQYKILNCANYHLTQVRTDFYDEFWGQGLRAAPKKQKKHTLSLTPDTTLYNAAQIICAN
YGEAFSVDKK

A

B

Ysebaert C, Denoël P, Weynants W, Bakaletz LO, Novotny LA, Godfroid F, Hermand P. A Protein E-PilA fusion protein shows vaccine potential against nontypeable *Haemophilus influenzae* in mice and chinchillas. Infection and Immunity 87(8); 2019
doi: http://dx.doi.org/10.1128/IAI.00345-19

Ysebaert C, Denoël P, Weynants W, Bakaletz LO, Novotny LA, Godfroid F, Hermand P. A Protein E-PilA fusion protein shows vaccine potential against nontypeable *Haemophilus influenzae* in mice and chinchillas. Infection and Immunity 87(8); 2019 doi: http://dx.doi.org/10.1128/IAI.00345-19

Ysebaert C, Denoël P, Weynants W, Bakaletz LO, Novotny LA, Godfroid F, Hermand P. A Protein E-PilA fusion protein shows vaccine potential against nontypeable *Haemophilus influenzae* in mice and chinchillas. Infection and Immunity 87(8); 2019
doi: http://dx.doi.org/10.1128/IAI.00345-19

SEQUENCE LISTING

```
<160> NUMBER OF SEQ ID NOS: 1

<210> SEQ ID NO 1
<211> LENGTH: 160
<212> TYPE: PRT
<213> ORGANISM: Artificial
<220> FEATURE:
<223> OTHER INFORMATION: Haemophilus Influenzae

<400> SEQUENCE: 1

Met Lys Lys Ile Ile Leu Thr Leu Ser Leu Gly Leu Leu Thr Ala Cys
1               5                   10                  15

Ser Ala Gln Ile Gln Lys Ala Lys Gln Asn Asp Val Lys Leu Ala Pro
            20                  25                  30

Pro Thr Asp Val Arg Ser Gly Tyr Ile Arg Leu Val Lys Asn Val Asn
            35                  40                  45

Tyr Tyr Ile Asp Ser Glu Ser Ile Trp Val Asp Asn Gln Glu Pro Gln
    50                  55                  60

Ile Val His Phe Asp Ala Val Val Asn Leu Asp Lys Gly Leu Tyr Val
65                  70                  75                  80

Tyr Pro Glu Pro Lys Arg Tyr Ala Arg Ser Val Arg Gln Tyr Lys Ile
            85                  90                  95

Leu Asn Cys Ala Asn Tyr His Leu Thr Gln Val Arg Thr Asp Phe Tyr
            100                 105                 110

Asp Glu Phe Trp Gly Gln Gly Leu Arg Ala Ala Pro Lys Lys Gln Lys
            115                 120                 125

Lys His Thr Leu Ser Leu Thr Pro Asp Thr Thr Leu Tyr Asn Ala Ala
    130                 135                 140

Gln Ile Ile Cys Ala Asn Tyr Gly Glu Ala Phe Ser Val Asp Lys Lys
145                 150                 155                 160
```

IMMUNOGENIC COMPOSITION

This application is a § 371 of International Application No. PCT/EP2019/065974, filed 18 Jun. 2019, which claims the priority of U.S. Provisional Application No. 62/686,889, filed 19 Jun. 2018.

TECHNICAL FIELD

The present invention relates to the field of treatment or prevention of infections using engineered bacteriophages. In particular, the present invention discloses bacteriophages which are engineered to express antigens. The bacteriophage targets a commensal bacterium, inserts nucleic acid encoding antigens into the commensal bacterium which then releases antigen and optionally adjuvant, without killing the commensal bacterium. Such expressed antigens can prime an immune response against an infectious agent or other disease.

BACKGROUND

Bacteriophages have been known for many years having been discovered by Fredrick Twart in 1915 and Felix d'Herelle in 1917. They are viruses with DNA or RNA genomes that infect and replicate within bacteria. Bacteriophages can undergo lytic or lysogenic cycles within bacteria. During the lytic cycle, the bacteriophage genetic material is injected into a bacterium, where transcription, translation and replication take place, leading to the assembly and packaging of bacteriophage proteins and nucleic acids and eventually to lysis where many bacteriophage are released, ready to infect further bacteria. Some bacteriophages can also carry out a lysogenic cycle in which the bacteriophage genetic material is incorporated into a bacterial genome.

Bacteriophages are currently being tested in clinical studies for the treatment of bacterial infections. Pathogens such as *S. aureus, E. coli* and *P. aeruginosa* are being targeted. Wright A Clin Otolaryngol (2009) 34:349, describes a controlled clinical trail of a therapeutic bacteriophage preparation for the treatment of chronic otitis due to antibiotic-resistant *Pseudomonas aeruginosa*. Sarker S A et al. Virology (2012) 434:222 describes the administration of an oral T4-like phage cocktail to healthy adult volunteers from Bangladesh (ClinicalTrials.govidentifier: NCT01818206).

Engineered bacteriophages have been developed for multiple bacterial targets with the objective of elimination or reduction of bacterial load. Examples include; SASP gene delivery: a novel antibacterial approach. Fairhead H Drug News Perspect. (2009):197-203, Engineered Phagemids for Nonlytic, Targeted Antibacterial Therapies; Krom R J et al Nano Lett. (2015) 15, 4808-4813; Sequence-specific antimicrobials using efficiently delivered RNA-guided nucleases Citorik R J et al. Nature Biotechnology (2014) 32 1141, Exploiting CRISPR-Cas nucleases to produce sequence-specific antimicrobials, Bikard D. Nature Biotechnology (2014) 32 1146. Dedrick et al. *Nature Medicine* 25, 730-733 (2019) discloses Engineered bacteriophages for treatment of a patient with a disseminated drug-resistant *Mycobacterium abscessus*.

Moreover, engineered bacteriophage have also been developed as vaccines or for targeted delivery to kill cancer cells. However, such bacteriophages are not intended to infect bacteria (Therapeutic and prophylactic applications of bacteriophage components in modern medicine. Adhya S et al. Cold Spring Harb Perspect Med. (2014) 1 1, Killing cancer cells by targeted drug-carrying phage nanomedicines Bar H. et al. BMC Biotechnol. (2008) 37, Phage protein-targeted cancer nanomedicines Petrenko V A and Jayanna P K. FEBS Lett. (2014) 588:341).

With the growth of antibiotic resistance, it is important that further strategies are developed to treat or prevent bacterial infection. The present invention represents an advance in the use of engineered bacteriophages. The engineered bacteriophages of the invention target commensal bacteria, insert nucleic acid encoding at least one antigen containing a signal sequence resulting in the release of the expressed antigen from the commensal bacterium. The antigen is able to induce an immune response in the host carrying the commensal bacterium. Where the expressed antigen is released from the commensal bacterium, the immune response against the antigen is developed away from the commensal bacterium, ensuring that the immune response is specifically against antigen and does not affect the commensal bacteria. The antigen may be associated with any disease or pathogen against which an immune response is helpful.

Accordingly, there is provided, an engineered bacteriophage capable of binding to a commensal bacterium and inserting its genome polynucleotide into the commensal bacterium, but incapable of producing progeny, of carrying out a lysogenic cycle and/or a lytic cycle within the commensal bacterium, wherein the engineered bacteriophage comprises a phage genome polynucleotide including a gene encoding at least one heterologous antigen(s) under the control of a promoter, optionally wherein the gene encoding at least one heterologous antigen contains a signal sequence capable of driving the release of the heterologous antigen from the commensal bacterium.

In a further aspect of the invention there is provided an engineered bacteriophage genome polynucleotide comprising a heterologous antigen gene encoding a heterologous antigen under the control of a promoter wherein the heterologous antigen gene optionally comprises a signal sequence capable of driving the release of the heterologous antigen from a commensal bacterium, wherein at least one gene encoding a capsid protein is deleted, at least one gene encoding a lytic machinery protein is deleted and optionally at least one gene encoding a lysogeny machinery protein is deleted.

In a further aspect of the invention there is provided an engineered bacteriophage genome polynucleotide comprising a heterologous antigen gene encoding a heterologous antigen under the control of a promoter wherein the heterologous antigen gene optionally comprises a signal sequence capable of driving the release of the heterologous antigen from a commensal bacterium, wherein at least one gene encoding a capsid protein is not present, at least one gene encoding a lytic machinery protein is not present and optionally at least one gene encoding a lysogeny machinery protein is not present.

In a further aspect of the invention there is provided a use of the engineered bacteriophage or the engineered bacteriophage genome polynucleotide of the invention in the expression and optionally release of heterologous antigens from a commensal bacterium In a further aspect of the invention there is provided a pharmaceutical composition or a vaccine comprising the engineered bacteriophage or the engineered bacteriophage genome polynucleotide of the invention.

In a further aspect of the invention there is provided a engineered bacteriophage or a engineered bacteriophage genomic polynucleotide according to the invention, for use in the prophylactic prevention of disease, optionally infectious disease or cancer.

In an further aspect of the invention, there is provided a method of treatment of a disease comprising the steps of: a) administering the engineered bacteriophage of the invention or the engineered bacteriophage genomic polynucleotide of the invention, to a patient in need thereof such that the engineered bacteriophage or engineered bacteriophage genomic polynucleotide of the invention contacts a commensal bacterium; b) insertion of the genome polynucleotide into the commensal bacterium, and c) expression and release of the heterologous antigen at a sufficient level for an immune response to be elicited against the heterologous antigen.

BRIEF DESCRIPTION OF FIGURES

FIG. 4—Graph showing anti-ToxA immunogenicity in mice immunised with a fragment of the C-terminus of toxin A (aa 2387-2706), a fragment of the C-terminus of toxin B (aa 1750-2360), or fusions 1, 2, 3, 4 or 5 of ToxinA and Toxin B.

FIG. 5—Graph showing hemagglutination inhibition in mice immunised with a fragment of the C-terminus of toxin A (aa 2387-2706), a fragment of the C-terminus of toxin B (aa 1750-2360), or fusions 1, 2, 3, 4 or 5 of ToxinA and Toxin B.

Figure 6:
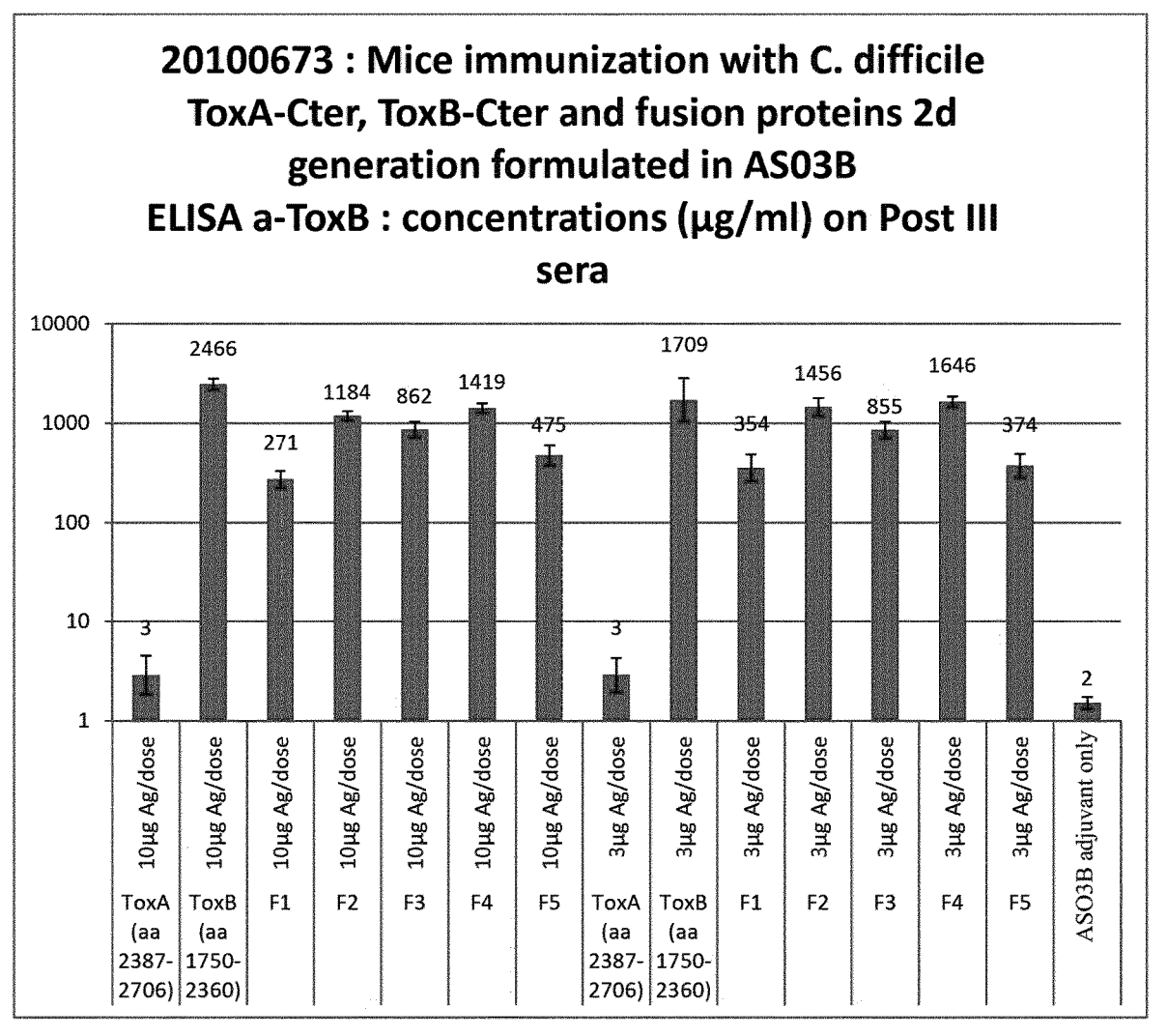

FIG. 6—Graph showing anti-ToxB immunogenicity in mice immunised with a fragment of the C-terminus of toxin A (aa 2387-2706), a fragment of the C-terminus of toxin B (aa 1750-2360), or fusions 1, 2, 3, 4 or 5 of ToxinA and Toxin B.

FIG. 7—Cyotoxicity inhibition titres from mice immunised with a fragment of the C-terminus of toxin A (aa 2387-2706), a fragment of the C-terminus of toxin B (aa 1750-2360), or fusions 1, 2, 3, 4 or 5 of ToxinA and Toxin B.

FIG. 8—Engineered bacteriophage genome use for the expression of PE antigen. A shows a schematic of the engineered bacteriophage genome. B shows the sequence of PE antigen (SEQ ID NO:1).

FIG. 9—Expression of PE antigen by *E. coli* bacteria exposed to engineered bacteriophage. Dot blots are shown in which the positive control is 200 ng of purified PE protein and the negative control is *E. coli* cells alone. Further samples contain lysed *E. coli* from kanamycin resistant colonies, all of which express PE.

FIG. 10.—Antibody levels after immunization. Mice (n=33/group) were immunized three times intramuscularly (IM) at a 2-week interval with 1 μg PilA, 1 μg PE, or 1 μg PE-PilA, adjuvanted with alum or AS01, or mice (n=20/group) were immunized three times intranasally (IN) at a 2-week interval with 6 μg PE, 6 μg PilA or 6 μg PE-PilA adjuvanted with the heat-labile toxin of *Escherichia coli* (LT). Sera were collected 14 days after the second and the third IM injection (days 28 and 42, respectively) or 14 days after the third IN injection (Day 42). PE-specific and PilA-specific antibody levels were measured by ELISA.

FIG. 11. Inhibition of vitronectin binding. Mice (n=33/group) were immunized intramuscularly on Days 0, 14 and 28 with 1 μg PE, 1 μg PilA or 1 μg PE-PilA formulated with alum or AS01. Sera were collected on Day 42 and a pool was made with all sera within each group. Twofold dilutions of these serum pools were used to inhibit the binding of vitronectin to PE in microtiter plates. Bound vitronectin was detected by specific antibody. The results were expressed as the dilution of serum able to inhibit 50% of vitronectin binding.

FIG. 12. Vaccine efficacy in an NTHi nasopharyngeal colonization model. Mice were immunized intranasally with LT-adjuvanted PE, PilA, PE-PilA or adjuvant alone (control) before they were intranasally challenged with NTHi strain 3224A. Bacterial colonies in nasal washings were counted on day 1 and day 2 post-challenge and expressed as log 10 mean cfu. Each symbol represents a mouse. Dashed lines indicate the limit of detection; Black horizontal bars are geometric means. Statistical analyses were carried out with ANOVA2. Groups were compared to each other over time (Tukey adjusted). Groups PE and PE-PilA versus control: $p<0.001$. Group PilA versus control: $p=0.9937$. Group PE versus group PE-PilA: $p=0.4239$. Representative experiment out of 4 with either 3224A or 3219C NTHi strain.

DETAILED DESCRIPTION

The present invention discloses a engineered bacteriophage capable of binding to (for example, adapted to bind to) a commensal bacterium but incapable of producing progeny within the commensal bacterium, wherein the engineered bacteriophage comprises a phage genome polynucleotide including a gene encoding at least one heterologous antigen(s) under the control of a promoter, wherein the gene encoding the at least one heterologous antigen optionally contains a signal sequence capable of driving the release of the heterologous antigen from the commensal bacterium. The phage genome polynucleotide contains a packaging sequence to allow the production of the engineered bacteriophage. The phage genome polynucleotide need contain no further bacteriophage genes. The phage genome polynucleotide optionally contains a phage origin of replication. The engineered bacteriophage typically comprises a viral head made up of capsid protein(s) and comprising a engineered phage genome polynucleotide, tail/plate structures containing means to bind to a commensal bacterial host cell and means to insert the engineered phage genome polynucleotide into a host cell. The genome polynucleotide is engineered to retain at least the packaging signal sequences and optionally sequences essential for genome replication, transcription and translation of the bacteriophage genome. However other parts of the bateriophage genome may be replaced with one or more genes encoding a heterologous antigen. It is preferred that the bacteriophage genome does not contain genes encoding proteins which allow the lysogenic cycle to proceed. It is also preferred that the bacteriophage genome of the invention does not contain all the genes that allow replication and release of viable bacteriophage. It is also preferred that the bacteriophage genome not encode the lytic machinery of the bacteriophage. Therefore genes that encode proteins involved with the initiation of the lysogenic cycle or that encode some of the structural proteins of the bacteriophage may be deleted and/or may be replaced with genes encoding at least one heterologous antigen. Optionally, the phage genome polynucleotide contains a packaging sequence and no further genetic material originating from a phage. The packaging signal allows an engineered phage to be made by inserting the genome polynucleotide containing the packaging sequence as well as at least one heterologous antigen gene under the control of a promoter, into a phage particle. Optionally, the engineered bacteriophage comprises a receptor for a commensal bacterium. This is typically a protein from the tail of the bacteriophage which binds specifically to a commensal bacterium, allowing the bacteriophage to bind to the commensal bacterium and insert genome polynucleotide into the commensal bacterium.

Figure 1:
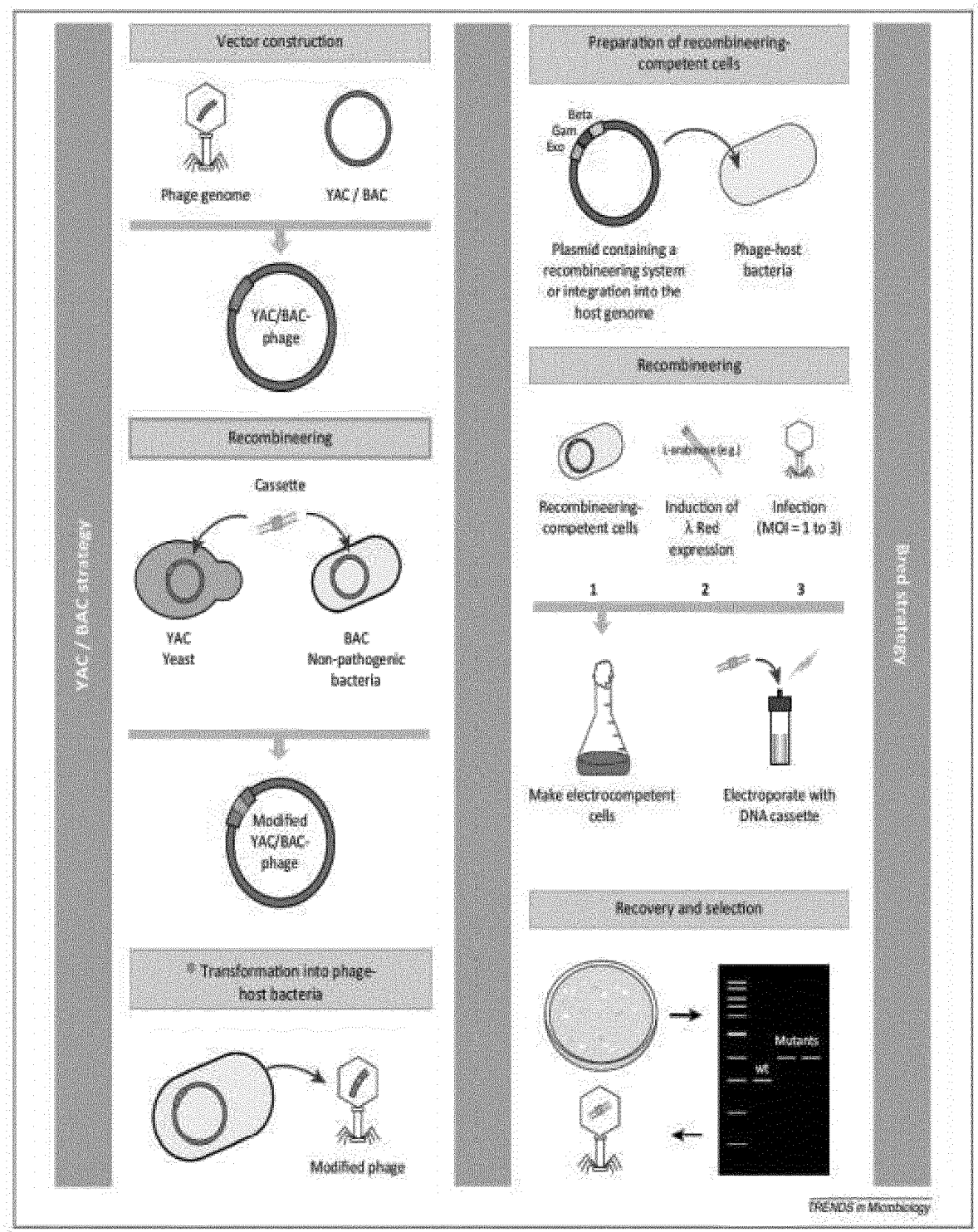
FIG. 1—demonstrates strategies for generating the engineered bacteriophage of the invention FIG. 2—demonstrates possibilities for the genetic engineering of the engineered bacteriophage.

By "heterologous antigen" it is meant that the heterologous antigen is an antigen that is not present in the wild-type bacteriophage. It may be an antigen from a different bacterium, for example a pathogenic bacterium or it may be an antigen from a virus or from a fungus. The antigen is a protein, glycoprotein, lipoprotein or even a saccharide synthesized by encoded enzymes.

By "heterologous pathogen" it is meant a pathogen which is not a bacteriophage.

The term "commensal bacterium" refers to a bacterium which is normally present in the subject to be treated and is not associated with a pathogenic infection.

In an embodiment of the invention the engineered bacteriophage is adapted to bind to the commensal bacterium and insert the bacteriophage genome polynucleotide into said host bacterium. For example, the engineered bacteriophage is adapted to bind to a commensal bacterium through modification of a gene encoding a bacteriophage tail fibre/plate. In such an embodiment, the gene encoding the tailfibre/plate is optionally mutated or substituted to increase the binding of the tailfibre/plate to a selected commensal bacterium. In other embodiments, a bacteriophage which naturally has high affinity for the commensal bacterium is selected and further engineered modifications, as set out in this application, are made to adapt the engineered bacteriophage to produce heterologous antigen in a commensal bacterium.

In an embodiment, the commensal bacterium is a part of skin, genital, oral or gut microbiome. For example, the commensal bacterium is *Propionibacterium acnes, Staphylococcus epidermidis, Lactobacillus, Streptococcus gordonii* or *Escherichia coli*. The invention includes the targeting of an *E. coli* bacterium as part of the gut microbiome, *S. epidermidis* or *P. acnes* as part of the skin microbiome, *Lactobacillus* as part of the genital microbiome or *Streptococcus gordonii* as part of the oral microbiome.

In an embodiment of the invention, the commensal bacterium is a commensal bacterium found in the intestine, on the skin or in the mouth. Examples of suitable commensal bacteria include staphylococcal, streptococcal, *E. coli, P. acnes*, or *Staphylococcus epidermidis* bacterium.

In an embodiment, the engineered bacteriophage targets a commensal bacterium in the intestine, for example an *E. coli* bacterium. In the case of the commensal *E. coli* bacteria, the caudovirales are able to bind to the commensal *E. coli* and insert a genome polynucleotide into the *E. coli*. The Caudovirales is comprised of three phylogenetically-related families that are discriminated by tail morphology: Myoviridae have long contractile tails, Siphoviridae have long non-contractile tails ad Podoviridae have short tails, Examples of *E. coli* bacteriophages are the coliphages λ (Siphoviridae), T4 (Myoviridae) and T7 (Podoviridae).

In an embodiment, the engineered bacteriophage of the invention targets a commensal bacterium on the skin, for example *S. epidermidis* or *P. acnes*.

In an embodiment, the engineered bacteriophage contains a gene encoding the heterologous antigen which is under the control of an early promoter or a strong promoter. Examples of a suitable promoter include a promoter controlling the expression of bacteriophage capsid proteins, optionally the promoter controlling the expression ot bacteriophage capsid protein from the original bacteriophage. Alternative strong promoters include promoters from the commensal bacterium which drive the expression of high expression level proteins. This can be simply accomplished by replacing the gene encoding capsid proteins with the gene encoding the heterologous antigen in the engineered bacteriophage. Alternatively a capsid promoter or another promoter, such as a strong promoter can be engineered to a position adjacent to the heterologous antigen genes.

In an embodiment, the engineered bacteriophage of the invention is selected from the group of families consisting of; myoviridae, siphoviridae, podoviridae, corticiviridae, tectiviridae, leviviridae, cystoviridae, inoviridae, lipothrixviridae, rudiviridae, plasmaviridae and fuselloviridae. Of these, myoviridae or a siphoviridae or a podoviridae are preferred. In an embodiment the engineered bacteriophage is a engineered lamda coliphage.

In an embodiment, the heterologous antigen gene contains a signal sequence which directs the protein to be released from the commensal bacterium, either by secretion or excretion (Bacterial Secretion Systems—An Overview Erin Green and Joan Mecsas, Microbiol. Spectr. 2016 February; 4(1): doi:10.1128/microbiolspec.VMBF-0012-2015). Examples of suitable signal sequences include type I, II, III, IV or V signal sequences of bacteria. Depending on the choice of commensal bacterium and the choice of antigen, the skilled person is able to determine an appropriate signal sequence to use to accomplish efficient release of the heterologous antigen.

Typical examples include co-translational secretion using a DsbA singal sequence, post-translational secretion using a PelB, OmpA or OmpX signal sequence, Tata secretion pathway using a YdcG, Sufl or Yack signal sequence.

In an embodiment, the heterologous antigen is a bacterial protein originating from a Gram positive or Gram negative bacterium, for example a protein capable of generating an effective immune response against a pathogenic bacterium.

In an embodiment wherein the engineered bacteriophage targets a commensal bacterium located in the intestine, the heterologous antigen protein is a protein capable of generating an immune response against a pathogenic bacterium of the human intestine. For example, the heterologous antigen is optionally a protein from *C. difficile, Heliobacter pylori, Shigella* or ETEC *E. coli*.

Examples of *Clostridium difficile* proteins which can be encoded by the engineered bacteriophage include protein comprising at least part of the repeat domain of Toxin A and/or Toxin B of *C. difficile*. It is preferred that the fragments of ToxinA and/or Toxin B are not toxic. In particular, fusion proteins containing part of the repeat domain of Toxin A and Toxin B are disclosed in WO 00/61762, EP2753352, U.S. Pat. No. 9,409,974, WO 12/163817, WO 12/163811 and fusion proteins disclosed in these publications are suitable for use as heterologous antigens of the invention. Further *C. difficile* antigens that can be used as heterologous antigen are binary toxin (CdtA and/or CdtB WO 15/197737) other *C. difficile* proteins disclosed in WO 14/045226 or WO 15/61529.

In other embodiments, the engineered bacteriophage of the invention contains a gene encoding a heterologous antigen protein that is a viral protein or a fungal protein.

In an embodiment, the heterologous antigen is a staphylococcal, streptococcal, *Shigella, Pseudomonas, Propionibacterium, Acinetobacter* or meningococcal antigen or an antigen from *E. Coli, H. pylori, P. aeruginosa, C. difficile, P. acnes, K. pneumoniae, N. gonorrhaea*.

In an embodiment, the engineered bacteriophage of the invention comprising a phage genome polynucleotide including at least 2, 3, 4, 5, 6, 7, 8, 9 or 10 genes encoding at least 2, 3, 4, 5, 6, 7, 8, 9 or 10 heterologous antigens. These genes are optionally added to the genome polynucleotide at the same position as the deletion of other genes from the genome polynucleotide. Since the capsid proteins are under the control of a strong promoter, one option is to replace the capsid protein gene(s) with one or more heterologous protein antigens, whose expression is driven by the strong promoter. Further or alternatively, genes encoding lytic cycle or lysogeny genes can be replaced by one or more heterologous antigen encoding genes. In an embodiment, the phage genome polynucleotide contains at least one packaging signal and at least, 1, 2, 3, 4, 5, 6, 7, 8, 9 or 10 heterologous antigens under the control of a promoter, for example a strong promoter.

It is preferred that the engineered bacteriophage does not lyse the commensal bacterium, so that antigen production and release from the commensal bacterium can continue. Therefore, it is preferred that the engineered bacteriophage does not contain genes encoding proteins which would either lyse the commensal bacterium or act as a antibacterial toxin, for example non-lytic antimicrobial peptides (AMPs) are not encoded by the genome polynucleotide.

A further aspect of the invention is the genetic material of the engineered bacteriophage. The invention therefore provides, an engineered bacteriophage genome polynucleotide comprising a heterologous antigen gene encoding a heterologous antigen under the control of a promoter wherein the heterologous antigen gene optionally comprises a signal sequence capable of driving the release of the heterologous antigen from a commensal bacterium, wherein at least one gene encoding a capsid protein is deleted, at least one gene encoding a lytic machinery protein is deleted and optionally at least one gene encoding a lysogeny machinery protein is deleted.

The invention also provides, an engineered bacteriophage genome polynucleotide comprising a packaging signal sequence and a heterologous antigen gene encoding a heterologous antigen under the control of a promoter wherein the heterologous antigen gene optionally comprises a signal sequence capable of driving the release of the heterologous antigen from a commensal bacterium, wherein no gene encoding a capsid protein is present, no gene encoding a lytic machinery protein is present and no gene encoding a lysogeny machinery protein is present.

In an embodiment, the invention discloses an engineered bacteriophage genome polynucleotide comprising a packaging signal sequence, a phage origin of replication and a gene encoding a heterologous antigen under the control of a promoter which comprises a signal sequence capable of releasing the heterologous antigen from a commensal bacterium.

In an embodiment, the invention discloses an engineered bacteriophage genome polynucleotide comprising a packaging signal sequence, a phage origin of replication, a bacterial origin of replication and a gene encoding a heterologous antigen under the control of a promoter which comprises a signal sequence capable of releasing the heterologous antigen from a commensal bacterium.

In an embodiment, the invention discloses an engineered bacteriophage genome polynucleotide comprising a packaging signal sequence, a phage origin of replication, a bacterial origin of replication, a selection marker and a gene encoding a heterologous antigen under the control of a promoter which comprises a signal sequence capable of releasing the heterologous antigen from a commensal bacterium.

In an embodiment, the invention discloses an engineered bacteriophage genome polynucleotide comprising a packaging signal sequence, a phage origin of replication, a bacterial origin of replication and a gene encoding a heterologous antigen under the control of a promoter which comprises a signal sequence capable of releasing the heterologous antigen from a commensal bacterium and does not contain a gene encoding a phage capsid protein.

In an embodiment, the invention discloses an engineered bacteriophage genome polynucleotide comprising a packaging signal sequence, a phage origin of replication, a bacterial origin of replication and a gene encoding a heterologous antigen under the control of a promoter which comprises a signal sequence capable of releasing the heterologous antigen from a commensal bacterium and does not contain a gene encoding a phage capsid protein nor a gene encoding a lytic machinery protein.

In an embodiment, the invention discloses an engineered bacteriophage genome polynucleotide comprising a packaging signal sequence, a phage origin of replication, a bacterial origin of replication and a gene encoding a heterologous antigen under the control of a promoter which comprises a signal sequence capable of releasing the heterologous antigen from a commensal bacterium and does not contain a gene encoding a phage capsid protein nor a gene encoding a phage lytic machinery protein nor a gene encoding a phage lysogeny machinery protein.

In an embodiment, the engineered bacteriophage or the engineered bacteriophage genome polynucleotide does not contain a gene encoding a phage capsid protein and/or a phage lytic machinery protein and/or a phage lysogeny machinery protein. For example, the engineered bacteriophage or the engineered bacteriophage genome does not contain a gene encoding a phage capside protein; the engineered bacteriophage or the engineered bacteriophage genome does not contain a gene encoding a phage lytic machinery protein; the engineered bacteriophage or the engineered bacteriophage genome does not contain a gene encoding a phage lysogeny machinery protein; the engineered bacteriophage or the engineered bacteriophage genome does not contain a gene encoding a phage lytic machinery protein or a phage lysogeny machinery protein; the engineered bacteriophage or the engineered bacteriophage genome does not contain a gene encoding a phage capsid protein or a phage lytic machinery protein; the engineered bacteriophage or the engineered bacteriophage genome does not contain a gene encoding a phage capsid protein or a phage lysogeny machinery protein; or the engineered bacteriophage or the engineered bacteriophage genome does not contain any of a gene encoding a phage capsid protein or a phage lytic machinery protein or a phage lysogeny machinery protein.

In an embodiment, an engineered bacteriophage incapable of producing progeny has a genome polynucleotide that does not encode a bacteriophage capsid protein.

In an embodiment, an engineered bacteriophage that is incapable of carrying out a lysogenic cycle has a genome polynucleotide that does not encode a phage lysogeny machinery protein.

In an embodiment, an engineered bacteriophage that is incapable of carrying out a lytic cycle has a genome polynucleotide that does not encode a phage lytic machinery protein.

In an embodiment, an engineered bacteriophage that is adapted to bind to the commensal bacteriophage contains a tail fibre/plate which binds to a commensal bacterium. Optionally, the tail fibre/plate has a mutated sequence and optionally, the mutated sequence increases binding of the engineered bacteriophage to a commensal bacterium.

The genome polynucleotide of the invention encodes at least 1 (for example 1, 2, 3, 4, 5, 6, 7, 8, 9, or 10) heterologous antigen(s) and its/their expression is driven by at least one promoter such that the commensal bacterium produces sufficient heterologous antigen protein for an immune response to be elicited against the heterologous antigen. The gene encoding the/each heterologous antigen contains a signal peptide that drives the release of the heterologous antigen from the commensal bacterium, allowing the heterologous antigen to encounter the immune system of the host (for example a human) at a distance from the commensal bacterium so that the commensal bacterium is not targeted by the host immune response. The absence of genes encoding capsid protein, lytic machinery and lysogeny machinery proteins leads to the engineered bacteriophage being unable to carry out the production of progeny, a lytic cycle or a lysogenic cycle within the commensal bacterium. The commensal bacterium therefore continues to release heterologous antigen so that a robust immune response is elicited against the heterologous antigen. In an embodiment, the heterologous antigen elicits an immune response which is effective against a pathogen found in the vicinity of the commensal bacterium.

In an embodiment, the genome polynucleotide retains an origin of replication so that the genome polynucleotide can be replicated within the commensal bacterium. For example, in a high-copy number example 500-700 copies of the genome polynucleotide can be found in a commensal cell, in a medium-copy number genome polynucleotide 20-100 copies of the genome polynucleotide are found in a commensal bacterium whereas for a low-copy number bacterial polynucleotide 5-20 copies are found in a commensal bacterium. An increased number of copies allows higher levels of transcription/translation of a heterologous antigen and the release of higher levels of heterologous antigen from the commensal bacterium.

In an embodiment, the gene encoding the heterologous antigen is under the control of a strong promoter. For example, the heterologous antigen is under the control of the promoter associated with the production of capsid protein. This can be achieved by substituting the capsid protein gene for a heterologous antigen gene. Other strong promoters are readily available to the skilled person, for example promoters driving the production of proteins having a high expression level in the commensal bacterium.

In an embodiment, the engineered bacteriophage genome polynucleotide of the invention is engineered from a bacteriophage genome polynucleotide from the group of families consisting of; myoviridae, siphoviridae, podoviridae, corticiviridae, tectiviridae, leviviridae, cystoviridae, inoviridae, lipothrixviridae, rudiviridae, plasmaviridae and fuselloviridae. For example, from a myoviridae or a siphoviridae or a podoviridae genome polynucleotide.

In an embodiment where *E. coli* is used as the commensal bacterium, the engineered bacteriophage genome polynucleotide is suitably engineered from a T4, T7 or lamda coliphage genome polynucleotide.

In an embodiment, the genome polynucleotide is engineered to delete all genes encoding a capsid protein. In an embodiment, the engineered bacteriophage genome polynucleotide is engineered to delete all genes encoding lytic machinery proteins. In an embodiment, the engineered bacteriophage genome polynucleotide is engineered to delete all genes encoding lysogeny machinery proteins. When deciding how many genes to delete, it should be borne in mind that the size of the genome polynucleotide should be kept at about the same size before and after engineering. Therefore where more or larger heterologous antigens are to be expressed, more no-essential genes should be deleted from the bacteriophage genome.

In an embodiment, the engineered bacteriophage genome polynucleotide retains the origin of replication so that replication of the bacteriophage genome polynucleotide can occur, leading to potentially higher levels of heterologous antigen expression.

In an embodiment, the origin of replication is deleted from the bacteriophage genome polynucleotide, leading to no replication of the genome polynucleotide. This may be appropriate where lower levels of heterologous antigen are required or where more control of the level of expression of the heterologous antigen is required.

In an embodiment, the engineered bacteriophage genome polynucleotide retains the origin a replication and all genes encoding proteins required to allow replication of the bacteriophage genome polynucleotide within a commensal bacterium.

Any heterologous antigen can be expressed in a commensal bacterium using the present invention. In an embodiment the heterologous antigen is associated with an infectious disease or with cancer. In an embodiment, the heterologous antigen protein is a viral protein or a fungal protein or a bacterial protein originating from a Gram positive or Gram negative bacterium. Where more than 1 (for example 2, 3, 4, 5, 6, 7, 8, 9 or 10) heterologous antigens are encoded, it is possible to express both viral and bacterial, or viral and fungal or bacterial and fungal or bacterial, viral and fungal heterologous antigen from the same commensal bacterium. This is particularly suitable to tackle infections like otitis media which contain both bacterial and viral elements.

In an embodiment, the heterologous antigen protein is a protein capable of generating an immune response against a pathogenic bacterium in the human gut. For example a *Clostridium difficile, H. pylori* or *Shigella* infection.

In an embodiment, the heterologous antigen is capable of generating an immune response against *C. difficile* infection. For example, the genome polynucleotide suitably comprises a gene encoding a protein capable of generating an immune response against *C. difficile*, for example *C. difficile* toxin A, *C. difficile* Toxin B, fragments of *C. difficile* Toxin A and/or *C. difficile* Toxin B or fusion proteins comprising fragments of *C. difficile* Toxin A and *C. difficile* Toxin B. In an embodiment, the genome polynucleotide comprises genes encoding one or more of the proteins disclosed in WO 12/163817, WO 12/163811, WO 14/96393, WO 15/197737 or WO 14/45226.

In an embodiment, the heterologous antigen is capable of generating an immune response against *Shigella, Salmonella, H. pylori* or pathogenic *E. coli*. In this case, the commensal bacterium is suitably a *E. coli* from the human gut.

In an embodiment, the heterologous antigen is a staphylococcal, streptococcal, *Shigella, Pseudomonas, Propionibacterium. acnes, Acinetobacter* or meningococcal protein or a protein from *E. Coli, P. aeruginosa, C. difficile, K. pneumoniae,* or *N. gonorrhoea* antigen.

In an embodiment, the heterologous antigen gene comprises a signal sequence which is capable of driving release of the heterologous antigen from the commensal bacterium by secretion or by excretion. The release of the heterologous antigen from the commensal bacterium after expression ensures that an immune response may be elicited against the heterologous antigen without the immune response being directed at the commensal bacterium. For example, a class I, II, III, IV or V signal sequence is attached to the heterologous antigen. The skilled person is aware of many signal sequences which would be suitable for use in a particular commensal bacterium or for a particular heterologous antigen.

In an embodiment, the engineered bacteriophage genome polynucleotide of the invention comprises a gene encoding an adjuvant. In an embodiment, the adjuvant is a TLR5 agonist; for example flagellin or a fragment thereof comprising at least 7, 10, 20, 30, 40, 50, 70, 100 or 200 continuous amino acids. In an embodiment, the more immunogenic epitopes (in the hypervariable region) of flagellin are removed to result in a fragment of flagellin which retains adjuvant activity but is less immunogenic (Nempont C et al J. Imunol. (2008) 181 (3) 2036-2043). Flagellin's hypervariable central region is not required for TLR5 agonist activity so deletion of this region allows adjuvant activity to be retained. For example for FliC (accession number AAL20871) the deletion of amino acids 204-292, 191-352 or 174-400 did not reduce TLR5 activity (Nempont C et al J. Imunol. (2008) 181 (3) 2036-2043).

In an embodiment, expression of the adjuvant is under the control of a strong promoter, for example the capsid protein promoter in the bacteriophage. In an embodiment, the adjuvant is expressed as a fusion protein with the heterologous antigen. For example, the gene encoding the heterologous antigen is fused to a gene encoding the adjuvant, optionally flaggellin (or fragment thereof) so that a single fusion protein is released from the commensal bacterium due to the signal peptide which forms part of the fusion protein gene.

In an embodiment, the engineered bacteriophage genome polynucleotide comprises a gene encoding a receptor for a commensal bacterium, which is optionally a tail fibre or a plate. Alternatively, the receptor for a commensal bacterium is not encoded by the engineered bacteriophage genome polynucleotide, in which case, the receptor for a commensal polynucleotide is encoded in a packaging cell line which is used in the production of the engineered bacteriophage.

In an embodiment, the heterologous antigen protein is not naturally expressed in a commensal bacterium that is infectable by the engineered bacteriophage.

In a preferred embodiment, engineered bacteriophage genome polynucleotide comprises a packaging signal.

In an embodiment, the engineered bacteriophage comprises a capsid, a genome polynucleotide, and a means of inserting its genome polynucleotide into a commensal bacterium wherein the genome polynucleotide contains at least one gene encoding at least one heterologous antigen under the control of a promoter, a packaging signal and a phage origin of replication.

In an embodiment, the engineered bacteriophage comprises a capsid, a genome polynucleotide, and a means of inserting its genome polynucleotide into a commensal bacterium wherein the genome polynucleotide contains at least one gene encoding at least one heterologous antigen under the control of a promoter, a packaging signal, a phage origin of replication and a bacterial origin of replication.

In an embodiment, the engineered bacteriophage comprises a capsid, a genome polynucleotide, and a means of inserting its genome polynucleotide into a commensal bacterium wherein the genome polynucleotide contains at least one gene encoding at least one heterologous antigen under the control of a promoter, a packaging signal, a phage origin of replication, a bacterial origin of replication and a selection marker.

A further aspect of the invention is a pharmaceutical composition comprising the engineered bacteriophage or the engineered bacteriophage genome polynucleotide of the invention. The pharmaceutical composition is optionally formulated as a topical treatment, or as a capsule or microcapsule for oral administration, wherein the engineered bacteriophage or the engineered bacteriophage genome polynucleotide is released in the intestine or is formulated as a mouth wash. A capsule or microcapsule formulation optionally contains chitosan-alginate, polymethacrylate copolymer or fatty acid.

A further embodiment of the invention is a pharmaceutical composition comprising the engineered bacteriophage or the engineered bacteriophage genome polynucleotide described above. In an embodiment, the pharmaceutical composition further comprises a pharmaceutically acceptable excipient, for example excipients to allow administration as a topical cream or ointment.

A further aspect of the invention is a vaccine comprising the engineered bacteriophage or the engineered bacteriophage genome polynucleotide of the invention.

The bacteriophage of the invention may be delivered as a pharmaceutical preparation, formulated for effective delivery to the required microbiome.

Where the engineered bacteriophage is required to reach the gut microbiome, microencapsulation is optionally used (WO 06/47871, CA2463827, Yongsheng Ma et al Applied and Environmental Micropbiology 74; 4799-4805 (2008)). Microencapsulation allows the engineered bacteriophage to be delivered orally and to be protected from the low pH associated with the stomach. Release occurs in the intestinal fluid where a pH of 6-7, for example 6.8 is achieved. In an embodiment, microencapsulation is microcapsules comprising chitosan-alginate, alginate, polymethacrylate copolymer, alginate-polymethacrylate or using skin milk and fatty acid. Suitable copolymers include anionic copolymers based on methacrylic acid and methyl methacrylate, for example the commercial product Eudragit S100. A lipoidal delivery system is optionally used, in which the engineered bacteriophage are entrapped in cationic lipic vesicles or liposomes.

Where the engineered bacteriophage is to be applied to the skin, the engineered bacteriophage is optionally formulated as a composition for topical treatment. In an embodiment, the engineered phage are combined with a pharmaceutically acceptable carrier, such as an excipient or stabiliser. Examples of pharmaceutically acceptable carrier, excipients and stabilisers include but are not limited to, buffers such as phosphate, citrate and other organic acids; antioxidants including ascorbic acid; low molecular weight polypeptides; protein such as serum albumin and gelatin; hydrophilic polymers such as polyvinylpyrrolidone; amino acids such as glycine, glutamine, asparagine, arginine or lysine; monosaccharides, disaccharides and other carbohydrates including glucose, mannose or dextrins; sugar alcohols such as mannitol or sorbitol; salt-forming counterions such as sodium.

The engineered bacteriophage may be formulated in a variety of product forms, for example a lotion, cream, spray, aerosol, aqueous buffer solution, gel, mask, foam and the like, for topical administration. In one embodiment, the phage are formulated as an aqueous solution of gel. The composition may include water, esters, isopropyl myristate and isopropyl palmitate; ethers such as dicapryl ether and dimethyl isosorbide; alcohols such as ethanol and isopropanol; fatty acids such as cetyl alcohol, cetearyl alcohol, stearyl alcohol and biphenyl alcohol; isoparaffins such as isooctane, isododecane and isohexadecane; silicone oils such as cyclomethicone, dimethicone, dimethicone crosspolymer, polysiloxanes and their derivatives e.g. organomodified derivatives; polyols such as propylene glycol, glycerine, butyene glycol, pentylene glycol, hexylene glycol; or any combinations of mixtures thereof. Aqueous vehicles may include one or more solvents miscible with water including lower alcohols, such as ethanol, isopropanol, and the like.

In an embodiment, the engineered bacteriophage composition is applied to a biocompatible substrate, for example a substrate comprising a natural fibre such as cotton, *eucalyptus*, bamboo filter or biocellulose or a combination thereof.

A further aspect of the invention is medical uses and methods of treatment for the engineered bacteriophage of the invention. Accordingly, there is provided a engineered bacteriophage comprising a phage genome polynucleotide including a gene encoding a heterologous protein, wherein the heterologous protein is not expressed as part of a phage coat/capsid protein, for use in the prophylactic prevention of infectious disease or other disease such as cancer. The infectious disease optionally comprises a bacterial, viral or fungal infection, for example a *C. difficile* infection.

Similarly there is provided a method of treatment comprising the steps of: a) administering a engineered bacteriophage comprising a phage genome polynucleotide including a gene encoding a heterologous protein, to a patient in need thereof such that the engineered bacteriophage contacts a bacterium; b) entry of the bacteriophage genome polynucleotide into the bacterium, and c) expression and release of the heterologous antigen at a sufficient level for an immune response to be elicited against the heterologous antigen.

The primary use of the engineered bacteriophage of the invention is for the treatment and/or prevention of disease, particularly infectious disease involving bacterial infection or disease involving bacterial and viral or bacterial and fungal components. The treatment and/or prevention of disease is preferably in a human. The engineered bacteriophage of the invention expresses at least one heterologous antigen at a level sufficient for an immune response to be elicited against the heterologous antigen. The heterologous antigen is secreted from the commensal bacterium such that the immune response elicited is against the heterologous antigen and not against the commensal bacterium. In this way, a infection is treated or prevented by using the commensal bacteria to make large amounts of a secreted antigen in the proximity of a pathogenic organism, against which an immune response is primed.

A further aspect of the invention is a vaccine comprising the engineered bacteriophage or the engineered bacteriophage genome polynucleotide of the invention.

A further aspect of the invention is an engineered bacteriophage according or a engineered bacteriophage genomic polynucleotide for use in the prophylactic prevention of infectious or non-infectious disease. Such a use comprises 1, 2, 3, 4, or 5 of the following steps: i) administering the engineered bacteriophage so that it contacts a commensal bacterium, and inserts the engineered bacteriophage genomic polynucleotide into the commensal bacterium, ii) optionally replication of the genomic polynucleotide within the commensal bacterium, iii) transcription and translation of at least one heterologous antigen, optionally as a fusion protein with an adjuvant, iv) release of the at least one heterologous antigen from the commensal bacterium without lysis of the commensal bacterium (e.g. through the action of a signal sequence) v) interaction with a host immune system to generate an immune response against the heterologous antigen. The heterologous antigen and adjuvant can have any of the properties described above. For example, the infectious or non-infectious disease can comprise a bacterial, viral or fungal infection, or any combination of these or cancer. In an embodiment, the commensal bacterium is *Propionibacterium acnes, Staphylococcus epidermidis, Lactobacillus, Streptococcus gordonii* or *Escherichia coli*; which are examples of commensal bacteria on the human skin microbiome, genital microbiome, oral microbiome or gut microbiome. In an embodiment, the disease is a bacterial infection, for example a *C. difficile* infection of the human gut.

In an embodiment, the use comprises steps i), iii), iv) and v). These steps may include any of the attributes set out above for the engineered bacteriophage or its genome polynucleotide.

A further aspect of the invention is a method of treatment of a disease comprising the steps of: a) administering the engineered bacteriophage or the engineered bacteriophage genomic polynucleotide of the invention, to a patient in need thereof such that the engineered bacteriophage or engineered bacteriophage genomic polynucleotide contacts a commensal bacterium; b) entry of the bacteriophage genome polynucleotide into the bacterium, and c) expression and release of the heterologous antigen protein at a sufficient level for an immune response to be elicited against the heterologous protein.

In an embodiment, the disease comprises a bacterial, viral or fungal infection. For example, the disease comprises a bacterial infection, for example *C. difficile* infection.

All references or patent applications cited within this patent specification are incorporated by reference herein.

In order that this invention may be better understood, the following examples are set forth. These examples are for purposes of illustration only, and are not to be construed as limiting the scope of the invention in any manner.

EXAMPLES

Example 1 Production of an Engineered Bacteriophage

To effectively produce the engineered bacteriophage the bacteriophage genome is inserted into a yeast artificial chromosome (YAC) or bacterial artificial chromosome (BAC) backbone that includes components for selection and replication in yeast or bacteria, respectively. Alternatively, any plasmid can be used to assemble the required elements of the engineered bacteriophage genome.

Alternatively, the phage genome can be engineered directly within the bacteria by using a recombineering competent bacteria (FIG. 1). For example as described in Nobrega F L. et al. Trends in Microbiology 2015 23:185.

Figure 2:
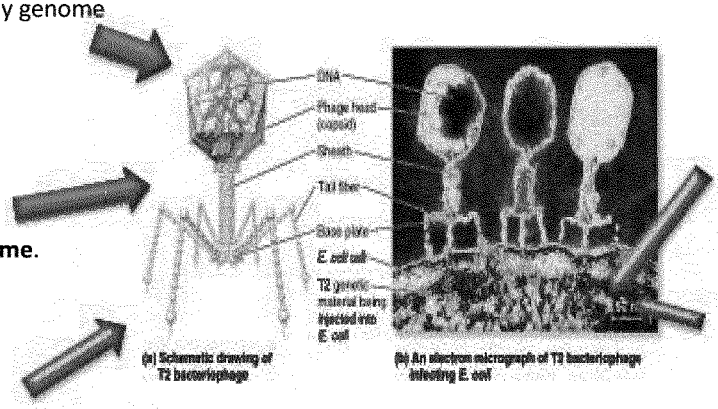

There are many possibilities for the genetic engineering of phage are shown in FIG. 2. Portions of the bacteriophage genome can be deleted to obtain a minimum synthetic bacteriophage genome which retains the sequences essential for transcription and translation and the packaging signal. Other gene including those encoding proteins involved in the lysogenic cycle and capsid proteins can be deleted and replaced with selected genes. The four possibilities disclosed in FIG. 2 include i) at least one heterologous antigen gene, under the control of a strong or early promoter to allow high enough levels of expression, and ii) a modified tail fibre/plate to allow the bacteriophage to infect the required range of commensal bacterial host cells. The selective removal and replacement of genes allows the bacteriophage genome to retain approximately the same size.

Figure 3:
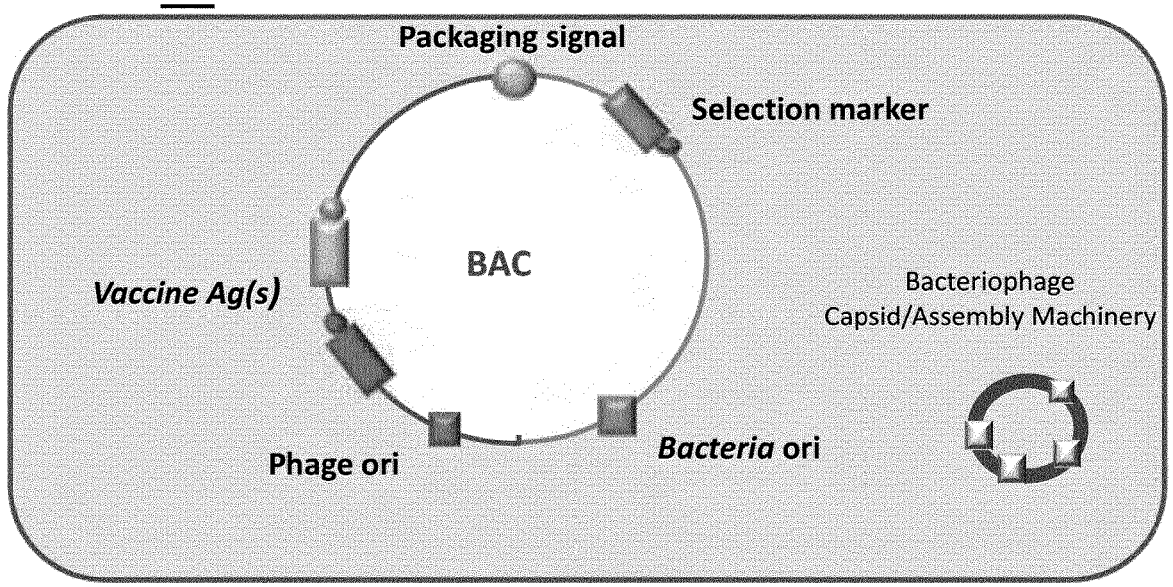
FIG. 3—demonstrates the intended use of engineered bacteriophages of the invention.
Figure 3:
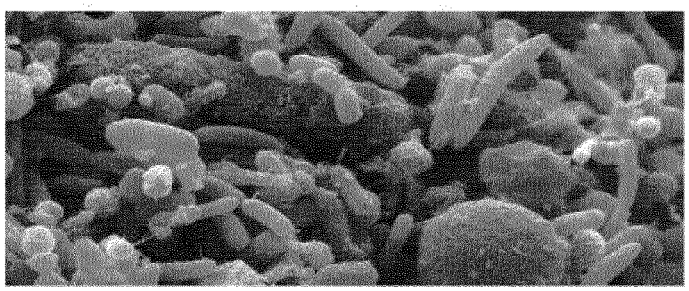

The engineered bacteriophage is based on a minimum phage genome that includes essential phage genome components such as origin of replication (ori), packaging signal(s) and phage tail recognition components in addition to several heterologous components. The first of these components is at least one gene that encodes a vaccine antigen driven by a early or strong promoter. The gene encoding a vaccine antigen contains a signal sequence which is designed to ensure that the vaccine antigen is secreted or excreted by the commersal host bacterium, thus ensuring that the resultant immune response is targeted against a pathogenic organism or antigen rather than against the commersal host bacterium. The engineered bacteriophage is missing some essential genes so will not be able to initiate a full lytic or lysogenic cycle when used in the treatment of a mammalian subject. However, it will be able to replicate in E. coli or other non-pathogenic bacterial cells which contain the bacteriophage capsid assembly machinery, as shown in FIG. 3. For example a BAC construct includes both the engineered bacteriophage components and the bacteria specific components (see FIG. 3).

Phage Amplification and Purification

The engineered bacteriophage is produced in commensal bacteria, for example E. coli that expresses the bacteriophage capsid machinery under an inducible or a constitutive promoter.

The bacterial host cell is transfected with a bacterial artificial genome (BAC) construct or appropriate artificial engineered bacteriophage genome. As the bacterial host cell expresses the capsid machinery in trans, the bacterial host cell is capable of producing phage in which the genome of the engineered bacteriophage is packaged into complete bacteriophage. The transfected bacterial host cell is cultured in a suitable medium, allowing phage replication to proceed in the bacterial host cells. The phage growth can be monitored using culture turbidity, pO2, pH, or may be allowed to continue for a pre-determined length of incubation time. Based on known phage life cycle parameters. Infected cells, concentrated by centrifugation, may be treated with organic solvents (e.g. chloroform), EDTA, lysozyme or bacteriophage lysins to induce lysis and release the phage. (Gill J J and Hyman P Current Pharmaceutical Biotechnology 2010 11:2-14).

After lysis, remaining cells or larger cell debris are removed by low-speed centrifugation and the phage containing supernatant is retained. The phage can then be purified by precipitation with polyethylene glycol (PEG) followed by removal of PEG by dialysis (Yamamoto et al (1970) 40; 734-744) or by passing through a 0.2 mm filter to remove cell debris and then using tangential flow filtration against a 100 kDa membrane which retains phage but allows passage of media components and some cellular proteins. This step is followed by scalable chromatography that can yield a recovery rate of up to 70% (Yamamoto et al (1970) 40; 734-744). Hydroxyapatite chromatography of phage display virions is described in Biotechniques (2005) 39; 879. T4 bacteriophage can be purified by using strong anion exchange monolithic chromatography columns (Smrekar F et al J. Chromotogr. B Analyt. Technol. Life. Sci. (2008) 861; 177-180).

Treatment of Disease Using Bacteriophage Adapted to Use Commensal Bacteria as Antigen Factories The overall goal of the treatment with engineered bacteriophage is to prevent acute or chronic bacterial disease and prevent disease relapse long term via persistent immunity.

Both in vitro & in vivo experiments are done to demonstrate that the bacteriophage concept is capable of producing vaccine antigen in the commensal host bacteria whilst allowing sufficient secretion of vaccine antigen to lead to the priming of an immune response against the chosen antigen. For in vitro demonstration the engineered bacteriophage will infect the commensal bacteria. The vaccine antigen is expressed under the control of a strong promoter so that sufficient antigen is produced and released from the commensal bacterium. The antigen is released from the commensal bacteria without compromising the viability of the commensal bacterium. The bacteriophage is incapable of producing viable bacteriophage progeny in the commensal host bacterium so that a single round of infection by the engineered bacteriophage leads to infection of sufficient commensal host bacteria and secretion of sufficient vaccine antigen for an effective immune response to be elicited. The amplification of the bacteriophage genome leads to the availability of further templates for transcription and translation of the vaccine antigens. These experiments therefore aim to demonstrate the potential to induce durable immunity.

An in vivo preclinical model using a bacteria as a pathogen is used to demonstrate the concept. The animals are treated with the engineered bacteriophage so that the initial cycle of vaccine antigen production takes place in the commensal bacteria and the antigens are released to prime an immune response. Blood sample are taken from the animals after 7-14 days so that immune responses against the vaccine antigen can be assessed. The induction of a protective immune response directed to the vaccine antigen is monitored by a suitable assay such as an ELISA on serum taken from the animal.

Subsequently the animals are challenged with the pathogen to evaluate protection provided by the vaccine antigen based on the reduction in pathogen load and/or the absence of disease symptoms.

To enhance the capacity of engineered bacteriophage to prime an immune response, the engineered bacteriophage genome may also contain a gene encoding an adjuvant such as a TLR5 agonist, a TLR3 agonist or flagellin, or a variant thereof (for example in which the hypervariable region is deleted Nempont et al J. Immunol. (2008) 181; 2036-2043). The adjuvant gene is under the control of a strong or early promoter and is expressed at the same time as the vaccine antigens. Both the vaccine antigen and adjuvant are released from the commensal bacterium due to the presence of signal sequences encoded in the vaccine antigen and adjuvant genes. The release of vaccine antigen and adjuvant allows the induction of an enhanced immune response, as demonstrated by appropriate assays such as ELISA or challenge models.

Example 2—Demonstration of Effectiveness of the Use of Commensal Bacteria in the Bacteriophage Driven Production of Antigen Both in vitro & in vivo experiments are done to demonstrate that engineered bacteriophage infect commensal bacteria, express the vaccine antigen and release sufficient antigen to elicit an effective immune response. A preclinical challenge model is used to demonstrate the capacity of the engineered bacteriophage to induce an immune response and protect against infection.

*Clostridium difficile* is used as the the model pathogen to demonstrate the concept. The *Clostridium difficile* ToxA/ToxB fusion protein (described in WO 12/163817) is selected as the vaccine antigen to demonstrate a preclinical proof of concept.

A bacteriophage genome is engineered in a BAC (or appropriate artificial engineered bacteriophage genome) such that it contains a tagged, detoxified toxin from *C. difficile* under the control of a strong early promoter, as the vaccine antigen. Other components of the bacteriophage genome are deleted so that the bacteriophage genome would not produce viable bacteriophage without the help of a host cell that contains bacteriophage capsid machinery. The BAC is transfected into *E. coli* that expresses the bacteriophage capsid machinery under an inducible or a constitutive promoter and cultured so that bacteriophage are produced. These are harvested and purified as described above.

The purified engineered bacteriophage are assessed in vitro for their ability to enter commensal *E. coli* and express a tagged *C. difficile* toxins in a commensal strain of *E. coli* infected by the engineered bacteriophage is assessed by Western blot using antibodies specific for the tagged *C. difficile* toxin.

Immunogenicity Model

C57BL/6 mice are treated with 1, 2 or 3 doses of microcapsulated engineered bacteriophage ($10^6$-$10^{12}$CFU) at 14-30 day intervals. Serum samples and faecal samples are taken 14 days after the first, second and third immunisations. Serum IgG and Faecal IgG are assessed by ELISA for the generation of an immune response against the *C. difficile* antigens expressed by the engineered bacteriophages. For example ELISAs for Toxin A and Toxin B are carried out.

After demonstrating that the engineered bacteriophage expresses *C. difficile* toxoid, the engineered bacteriophage is assessed in an in vivo model:

Challenge Model to Demonstrate Efficacy of Treatment:

C57BL/6 mice are treated with 1-3 doses of engineered bacteriophage ($10^6$-$10^{12}$ CFU) at days −42, −28 and −14 days prior to challenge with *C. difficile*. Prior to challenge, the mice are treated with antibiotics. The following antibiotics are added to drinking water from days −6 to −3 before challenge: kanamycine 0.4 mg/ml, gentamycine 0.035 mg/ml, colistine 850 U/ml, metronidazole 0.215 mg/ml, vancomycine 0,045 mg/ml. A further dose of Clindamycin 0.2 mg/100 μl is administered intraperitoneally at day −1. In addition, serum and faecal samples are taken the day before challenge and the level of serum IgG and faecal IgG against ToxA and ToxB, are measured by ELISA.

An oral Challenge dose: of $1.5 \times 10^6$ CFU/mouse (strain 6529) or $3 \times 10^3$ CFU/mouse (strain 43255) is administered. The mortality of the mice is followed between days 1 to 7 post challenge. In addition, colonization in faeces, caecum and colon is examined at days 1, 2, 3, 6 and 7 post challenge.

Expected Results

The bacteriophage treatment results in the generation of an immune response against *C. difficile* Toxin A and Toxin B, as measured by ELISA. It is expected that the generation of an immune response within the gut allows the generation of protection against the *C. difficile* challenge.

Example 3—Immunogenicity of Tox a or Tox B Fragments and ToxA-ToxB Fusions

A selection of fragments of Toxin A and Toxin B from *C. difficile* as well as fusion proteins containing elements of ToxinA and Toxin B (as described in WO 12/163817) were tested in a mouse model to ensure that they were immunogenic and could produce a neutralising immune response against the toxins.

Mice Immunization

Groups of 15 female Balb/c mice were immunized IM at days 0, 14 and 28 with 3 μg or 10 μg of the separate fragments of toxA and toxB as well as with ToxA-ToxB fusions proteins adjuvanted with AS03B. A control group of 10 mice was vaccinated with AS03B alone.

Anti-ToxA and anti-ToxB ELISA titers were determined in individual sera collected at day 42 (post III).

Hemagglutination inhibition titers were determined in pooled Post III sera.

Anti-ToxA and Anti-ToxB ELISA Response: Protocol

Samples of the toxA or toxB fragments were coated at 1 μg/ml in phosphate buffered saline (PBS) on high-binding microtitre plates (Nunc MAXISORP™), overnight at 4° C. The plates were blocked with PBS-BSA 1% for 30 min at RT with agitation. The mice anti-sera are prediluted 1/500 in PBS-BSA0.2%-TWEEN™ 0.05%. and then, further twofold dilutions were made in microplates and incubated at RT for 30 min with agitation. After washing, bound murine antibody was detected using Jackson ImmunoLaboratories Inc. peroxidase-conjugated affiniPure Goat Anti-Mouse IgG (H+L) (ref: 115-035-003) diluted 1:5000 in PBS-BSA0.2%-tween 0.05%. The detection antibodies were incubated for 30 min. at room temperature (RT) with agitation. The color was developed using 4 mg O-phenylenediamine (OPD)+5 μl $H_2O_2$ per 10 ml pH 4.5 0.1M citrate buffer for 15 minutes in the dark at room temperature. The reaction was stopped with 50 μl HCl, and the optical density (OD) was read at 490 nm relative to 620 nm.

The level of anti-ToxA or anti-ToxB antibodies present in the sera was expressed in mid-point titers. A GMT was calculated for the 15 samples in each treatment group (10 for the control group).

Hemagglutination Inhibition Assay: Protocol

Serial twofold dilutions of mice pooled antisera (25 μl) were performed in phosphate buffered saline (PBS) in 96-well U-bottom microplates.

25 μl of native Toxin A (0.2 μg/well) were then added and the plates were incubated at room temperature for 30 minutes.

After incubation, 50 μl of purified rabbit erythrocytes diluted at 2% were added to each well. The plates were incubated at 37° C. for 2 hours.

Plates were analysed visually, with hemagglutination presenting as diffuse red cells in the well and the inhibition of hemagglutination observed as a red point settled in the well.

The inhibition titers were defined as the reciprocal of the highest dilution of the serum inhibiting hemagglutination.

Cytotoxicity Assay

IMR90 fibroblast cells were cultured at 37° C. with 5% $CO_2$, in EMEM+10% fetal bovine serum+1% glutamine+1% antibiotics (penicillin-streptomycin-amphotericin) and were seeded in 96-well tissue culture plates at a density of $5 \cdot 10^4$ cells/well.

After 24 h, the cell media was removed from the wells.

Serial twofold dilutions of mice pooled antisera (50 μl) were performed in cell media.

50 μl of native Toxin B (0.5 ng/ml) is then added and the plates incubated at 37° C. with 5% $CO_2$ for 24 hours.

Cells were observed after 24 hours, and the proportion of rounded cells was determined.

The inhibition titers were defined as the reciprocal of the highest dilution of the serum inhibiting 50% cell rounding.

Results

Figure 4:
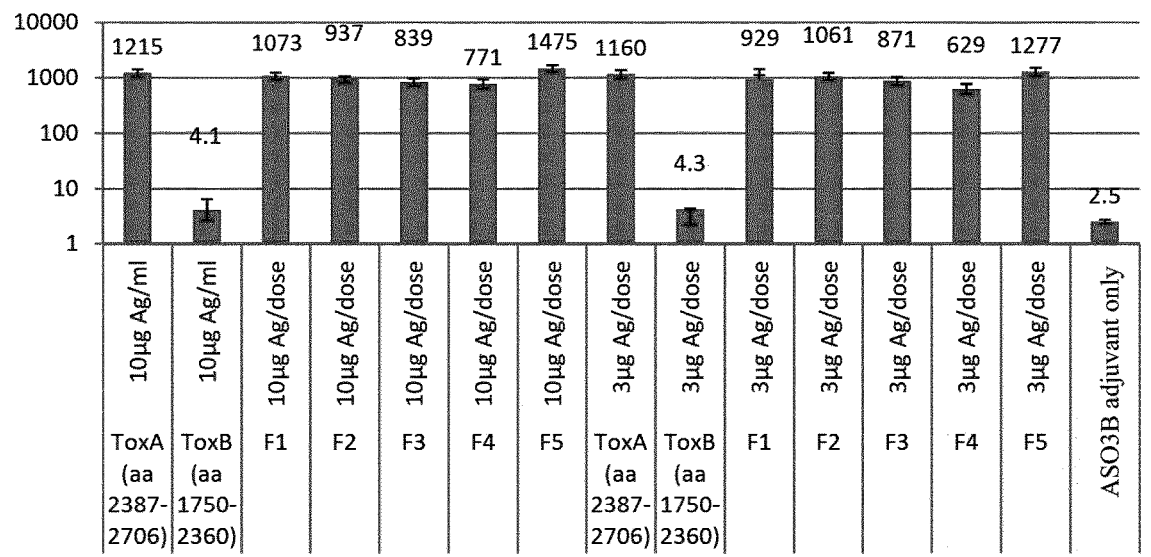
Figure 7:
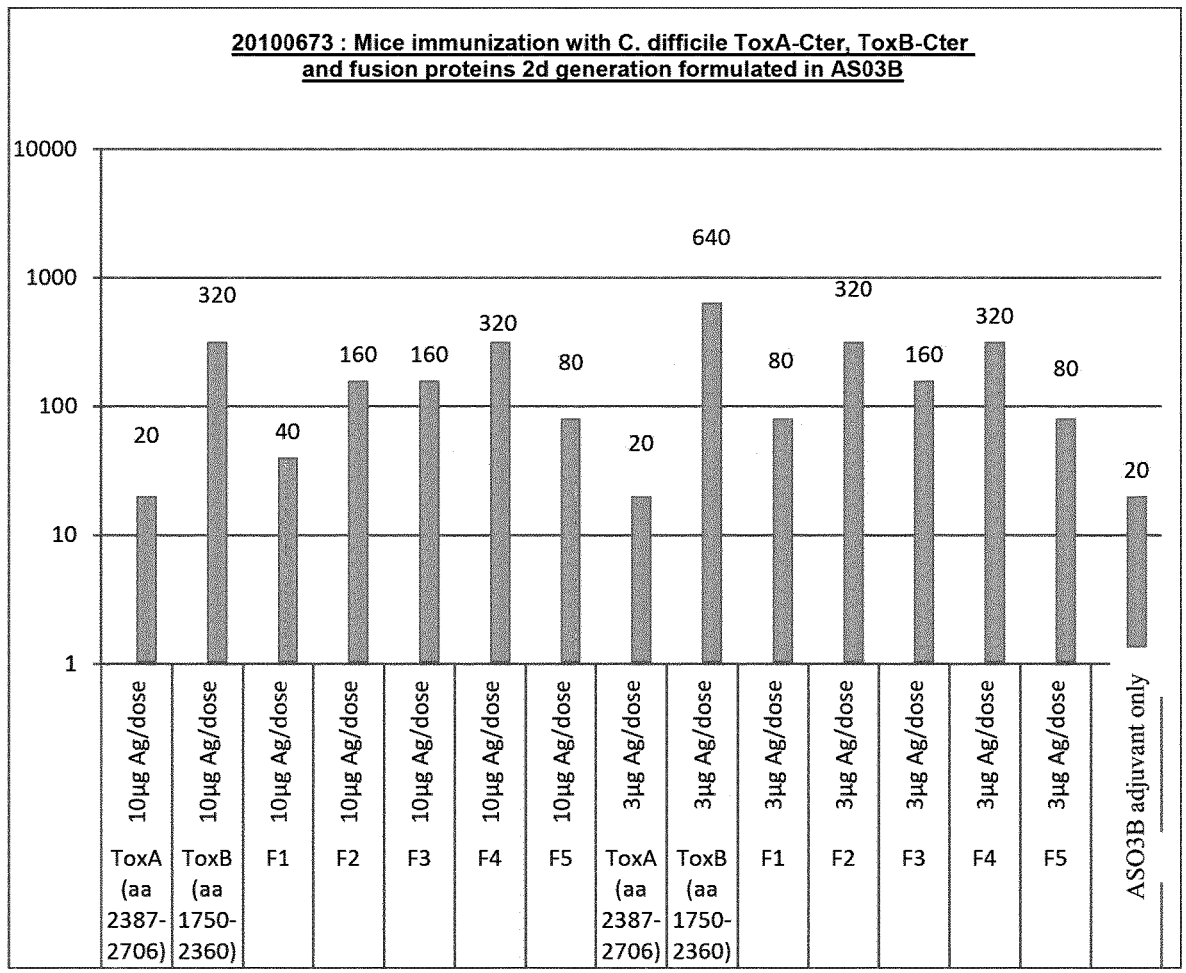
Figure 8:
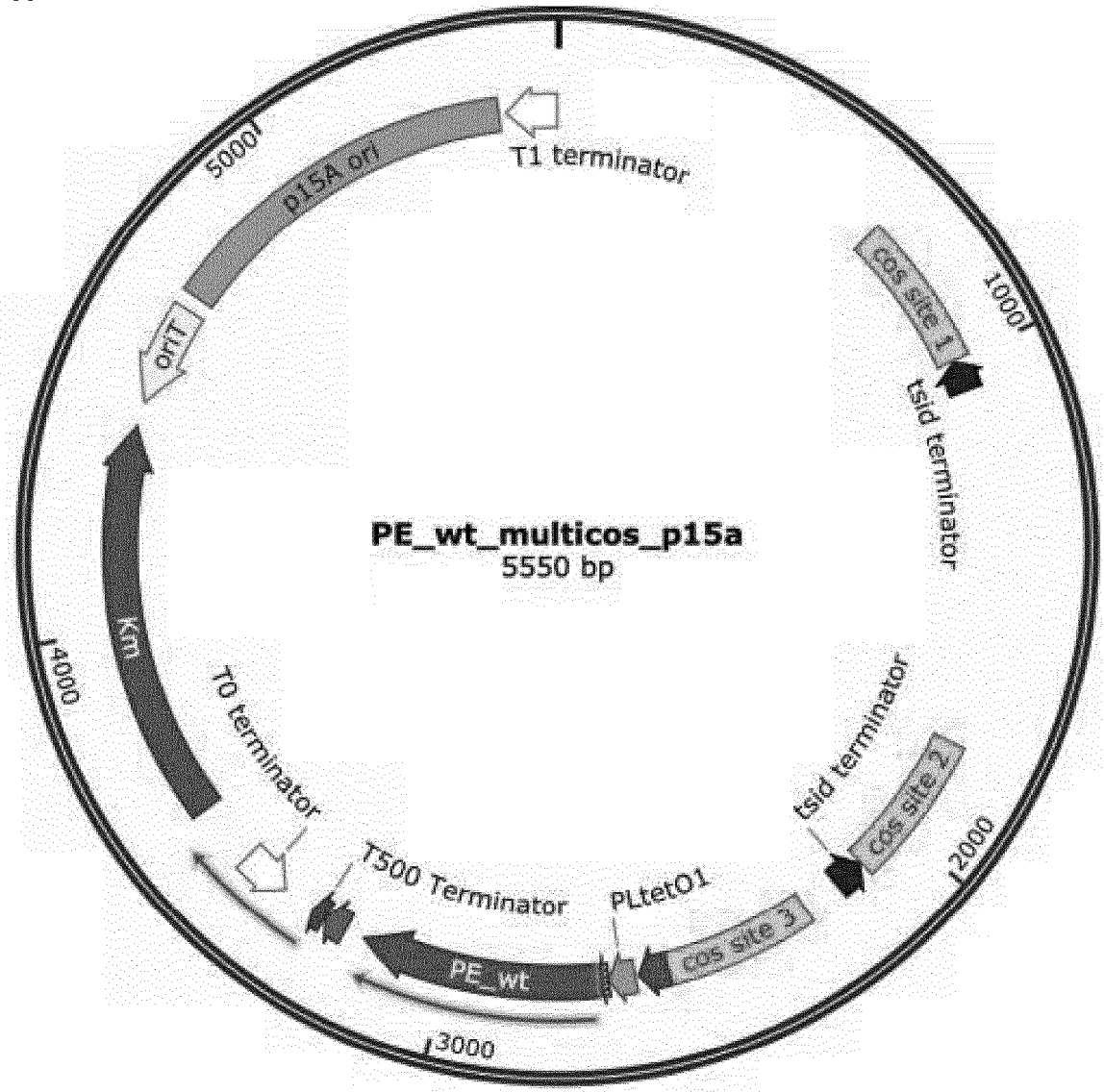
Figure 9:
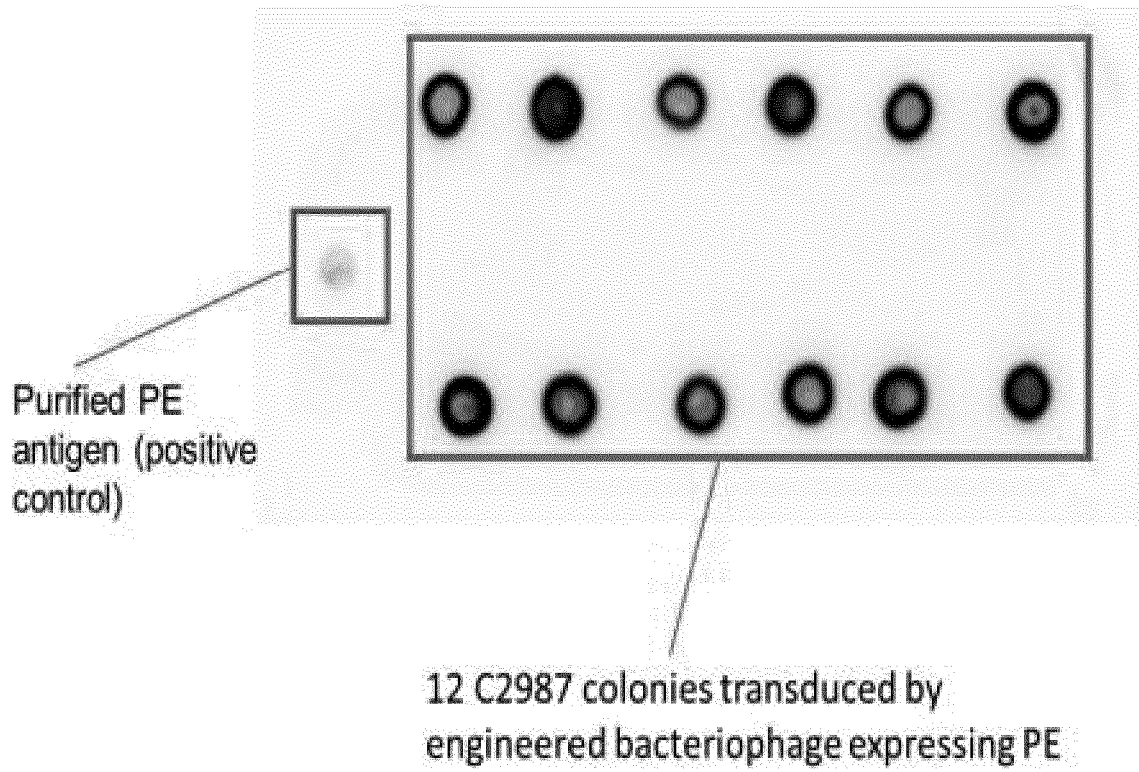
Figure 9:
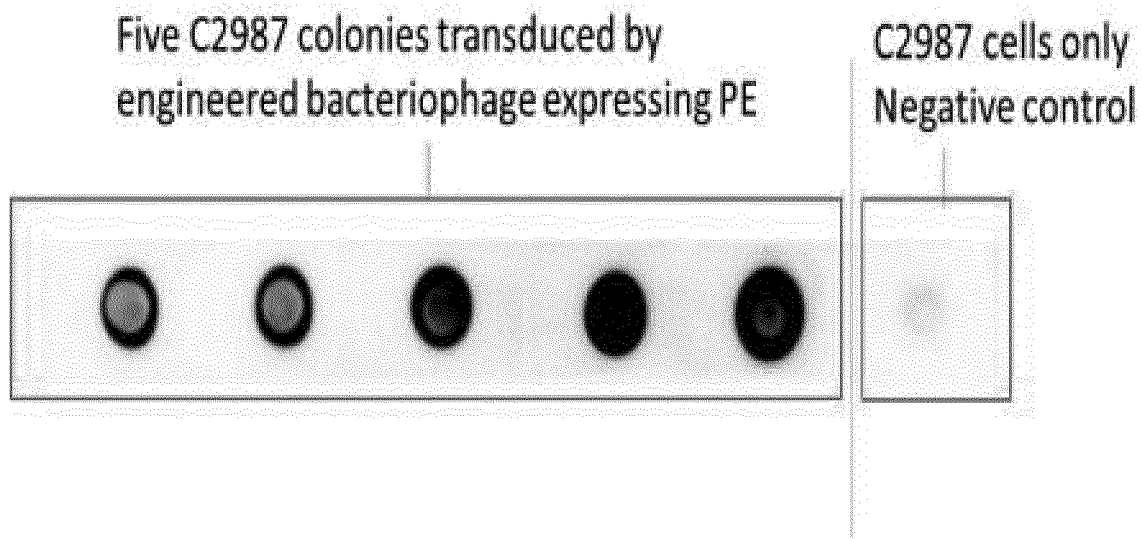

ELISA results, using Tox A antibodies are described in FIG. 4. Anti-Tox A antibodies were induced after immunization with the ToxA alone but also with each of the 5 fusions.

The functional properties of these antibodies were tested in the hemagglutination assay. This assay is only adapted for Tox A evaluation as no hemagglutination is observed with ToxB.

Haemagglutination inhibition titres are described in FIG. 5. Haemaglutination inhibition was observed with the anti-Tox A fragment sera or sera directed against each of the ToxA-ToxB fusions.

An ELISA using ToxB antibodies was also performed; the results of this are illustrated in FIG. 6. Anti-Tox B antibodies were induced after immunization with the ToxB fragment alone but also with the F2, F3 and F4 fusions.

Cytotoxicity inhibition titres are described in FIG. 7. Inhibition titers obtained using sera from mice immunised with the ToxB fragment or the ToxA-ToxB fusions were greater than that obtained using control sera.

Example 4

Expression of a Protein (PE) Following Transduction of *E. coli* Culture with an Engineered Bacteriophage Particle with a Synthetic Genome (Cosmid)

The plasmid shown in FIG. 8A was constructed including a gene encoding the PE protein shown in FIG. 8B, a kanamycin resistance gene, origins of replication (P15a) and cos sites to allow the packaging of the plasmid into hage capsids. Protein E (PE) is a ubiquitous antigen from non-encapsulated forms of *Haemophilus influenzae* (NTHi), described as important for the adhesion of the bacterium to epithelial cells (Ronander et al (2008) Microbes Infect 10:87-96. Protein E (PE) is known to bind to vitronectin, which protects the bacterium from complement attack (Singh et al (2013) Infect Immun 81:801-814.

- *E coli* C2987: is a non-pathogenic strain derived from of DH5α.
- KanR: kanamycin resistance
- $P2_{vir1}$: a mutant of bacteriophage P2 that is strictly lytic, used as a helper phage to provide P2 capsid proteins for the cosmid packaging.
- P15a: origin of replication
- Cos site: phage derived sequences essential for packaging into phage capsids.

The following experiment shows the ability of a bacteriophage to bind to and enter *E. coli* and to express a PE antigen under the control of a Tet01 promoter in *E. coli.*

Preparing Engineered Bacteriophage:

To produce bacteriophage particles, 20 ml of LB containing 2 mM CaCl2 was seeded with 0.5 ml of an overnight culture of *E coli* C2987 containing PE wt cosmid that was grown at 37° C. in presence of kanamycin (50 μg/mL). The culture was grown at 37° C. to OD600 of 1. The culture was infected with 10 μl of $P2_{vir1}$ ($10^{11}$) with MOI=0.1 and let to stand for 10 min at 37° C. The following reagents were added: $CaCl_2$) to a final concentration of 5 mM, $MgCl_2$ to a final concentration of 16 mM and glucose to a final concentration of 1%. The culture was shaken at 180-200 rpm at 37° ° C. for 1 hour and then EDTA was added to a final concentration of 10 mM. The culture was shaken at 250 rpm at 37° C. until lysis occurred (1-3 hours). 2 ml of chloroform was added and the mix was incubated at room temperature (RT) for 30 min whilst being shaken slowly. The mix was then centrifuged at 13000 rpm at RT for 10 minutes and the supernatant was collected and filtered through 0.2 μM membrane and stored at 4° C. The $P2_{vir1}$ titer checked on *E coli* C2987 was ~$10^{11}$-$10^{12}$.

Transduction with $P2_{vir1}$ Lysate and Engineered Bacteriophage Particles:

5 ml of an overnight culture of *E coli* C2987 cells were supplemented with $CaCl_2$) to a final concentration of 5 mM and were shaken at 37° C. for 15 minutes. 0.2 ml of the culture was taken and 0.2 ml of $P2_{vir1}$ lysate including the engineered bacteriophage particles (dilution for MOI=1) was added before incubating at 37° C. for 20 minutes with no shaking. 0.4 ml of 1M Na-citrate was added and mixed. 2.5-3 ml of Top agar 7 (TA7) pre-warmed at 42° C. were added, mixed and poured on the plate with Kanamycin (50 μg/mL). The plate was incubated overnight at 37° C. and around 300 Kanamycin resistant tranductants per plate was obtained.

Evaluation of the Expression of PE Antigen Following Transduction:

Ten *E. coli* C2987 transduced colonies were grown overnight at 30° C. in LB including Kanamycin (50 μg/mL). The OD600 of the overnight cultures was measured and they were diluted in 4% SDS in Tris pH6 according to the following formula: Volume of lysis buffer used to resuspend pellet from 1 mL of overnight culture (μL)=OD600/0.015 (This step is to normalise the number of cells from which protein is extracted). 1 mL of each culture was centrifuged at 12000 RCF. The resulting supernatants were discarded and the pellets were re-suspended and then heated to 95° C. for 10 minutes.

Dot blot was performed by spotting 2 μl of each sample onto nitrocellulose membrane and allowing the membrane to dry. As a positive control, 2 μl of 100 μg/ml PE antigen was used as presented in FIG. 9A. In FIG. 9B 2 μl of a negative control (non-tranduced *E coli*) was included in the dot blot. Non-specific binding was blocked by soaking the membrane in 5% BSA in TBS-T (20 mM Tris-HCl, 150 mM NaCl, 0.05% Tween 20, pH 7.5) for 30-60 minutes at room temperature. The membrane was then washed three times in TBS-T. The membrane was then incubated with an mouse monoclonal antibody against PE diluted in TBS-T containing 0.1% BSA for 30 minutes at room temperature. After washing three times in TBS-T, the membrane was incubated with an anti-mouse HRP conjugate for 30 minutes at room temperature. After washing three times in TBS-T and once with TBS, the membrane was incubated with ECL reagents and exposed to X-ray film to allow the detection of light.

Results

The results of the dot blot are shown in FIG. 9. As can be seen, all transducted *E. coli* colonies produced high levels of PE protein with darker spots being obtained in the transducted samples compared to the positive control which was loaded with 200 ng of PE protein.

Example 5—PE can Generate a Functional Immune Response in Mice

Immunization of Mice

Groups of 33 mice were immunized IM on Days 0, 14 and 28 with 1 μg PilA, 1 μg PE, or 1 μg PE-PilA adjuvanted with alum or AS01. Control injections consisted of alum or AS01 alone. The IgG levels directed against each antigen were determined by enzyme-linked immunosorbent assay (ELISA) in sera collected on Days 28 (Day 14 post-II) and 42 (Day 14 post-III).

ELISA

To determine anti-PE or anti-PilA IgG levels, microtiter plates were coated with PE or PilA (2 μg/mL or 4 μg/mL, respectively, in carbonate buffer) overnight at 4° C. After washing, serial two-fold dilutions of murine sera (starting at 1/500 for PE assay or 1/20-1/500 for PilA assay, depending on the experiment, in phosphate-buffered saline containing 0.05% Tween-20 [PBS-T]; 1 h at 25° C.) Afterwards, in both assays, peroxidase-conjugated goat anti-mouse IgG antibodies (Jackson laboratories code 115-035-003; 1/2500 or 1/1250 in PBS-Tween) were added for 1 h at 25° C. The colorimetric reaction was obtained by the addition of o-phenylenediamine dihydrochloride in citrate buffer in the presence of hydrogen peroxide for 15 min and stopped by addition of 1N HCl. Plates were read in a spectrophotometer at 490 and 620 nm. In both cases, an in-house calibrated reference serum was used and IgG concentrations (expressed as μg/ml) were calculated by the 4-parameter method using the Soft Max Pro software.

Inhibition of Vitronectin Binding

The sera collected on Day 42 for the determination of humoral responses were also used for the inhibition of vitronectin binding assay, which is a method to assess the functionality of anti-PE antibodies. A pool was made with all sera within each group. Vitronectin binding assay was carried out in microtiter plates. Plates were coated with PE (5 μg/mL in PBS) for 2 h at 37° C. After washing, saturation of the nonspecific binding sites was done by incubation with PBS-bovine serum albumin (BSA) 1%, and then two-fold serial dilutions of heat-inactivated immune murine sera (in PBS-T-BSA 0.02%) were added to the wells for overnight incubation at 4° C. After washing, vitronectin (Sigma-Aldrich SRP3186; 4 μg/mL) was added and incubated for 1 h at 37° C. Finally, after another washing step, bound vitronectin was detected by the addition of horseradish peroxidase-conjugated sheep anti-vitronectin antibodies (L12050350 C12120412; US Biologicals; 1/1000 in PBS-T for 30 min at 37° C.), followed by o-phenylenediamine dihydrochloride as described in the former paragraph. The mid-point titer (corresponding to the first dilution of murine sera able to inhibit 50% of binding) of each tested pool was determined.

Nasopharyngeal Colonization Model

For the nasopharyngeal colonization model, groups of 20 mice were immunized IN (10 μL in one nostril) on Days 0, 14 and 28 with 6 μg PE, PilA or PE-PilA, adjuvanted with LT (50 μg/mL; except at the third immunization). The IgG levels against each antigen were measured by ELISA in sera collected on Day 42 (Day 14 post-III). The animals were also challenged IN on Day 42 with $5 \times 10^6$ colony-forming units (cfu) of 3224A or 3219C NTHi strain (10 μL in one nostril). Full nasal cavities were dissected one and two days after the challenge, homogenized, and the resulting suspension cultured overnight at 37° C. on chocolate agar to determine bacterial load.

Statistical Analyses

Inhibition of vitronectin binding was analysed by ANOVA, followed by Tukey adjusted test. Vaccine efficacy in nasopharyngeal model was measured by ANOVA2 with groups and time as factors. Groups were compared to each other by Tukey adjusted test. Biofilms thickness and biomass were analysed by one-way ANOVA. For the passive transfer experiments, a sample size of n=10 allowed detection of 65% difference between two proportions (OM incidences) with a power of 80%, using a $\chi^2$ test. Four different statistical analyses were performed in each experiment to compare the vaccinated groups and the adjuvant control group, respectively on the proportion of animals developing OM (Fischer's exact test), the time to OM onset (first day of disease), the recovery time (last day of disease) and the area under the score curve. Results were considered significant when p values were equal to or below 0.05.

Results

Immunogenicity

ELISA tests were carried out on sera from mice immunised with PE.

Figure 10:
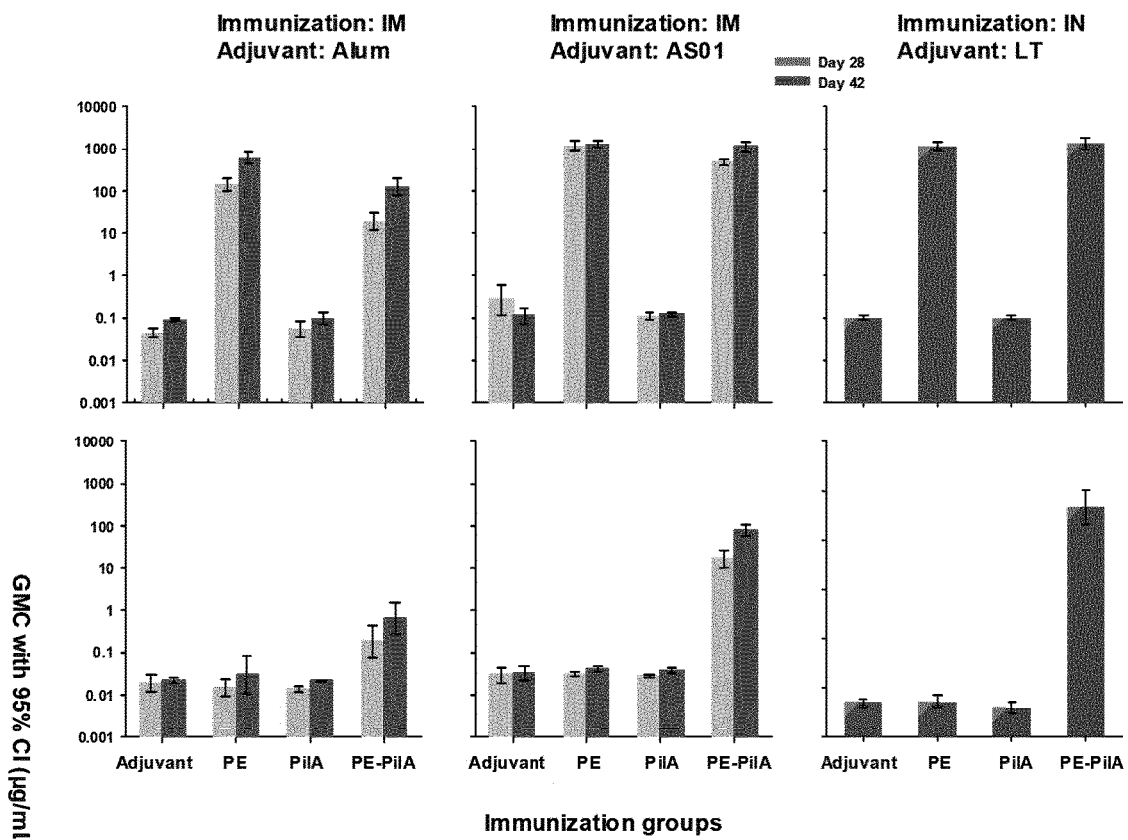

In mice, the humoral responses against PE after PE-PilA immunization were similar to those after immunization with PE alone, as evaluated on Day 42 (1106 μg/mL versus 1273 μg/mL, respectively, when given intramuscularly (IM) and adjuvanted with AS01, and 1349 μg/mL versus 1139 μg/mL when given intranasally (IN) and adjuvanted with the heat-labile toxin of *Escherichia coli* (LT), respectively). However, this was not the case when adjuvanted with alum (FIG. 10). In the latter case, although 100% of mice seroconverted after immunization with PE-PilA, the level of anti-PE antibodies was almost five times lower than after immunization with PE alone (126 μg/mL versus 608 μg/mL, respectively).

Inhibition of Vitronectin Binding by PE with Antibodies to PE-PilA Fusion

Figure 11:
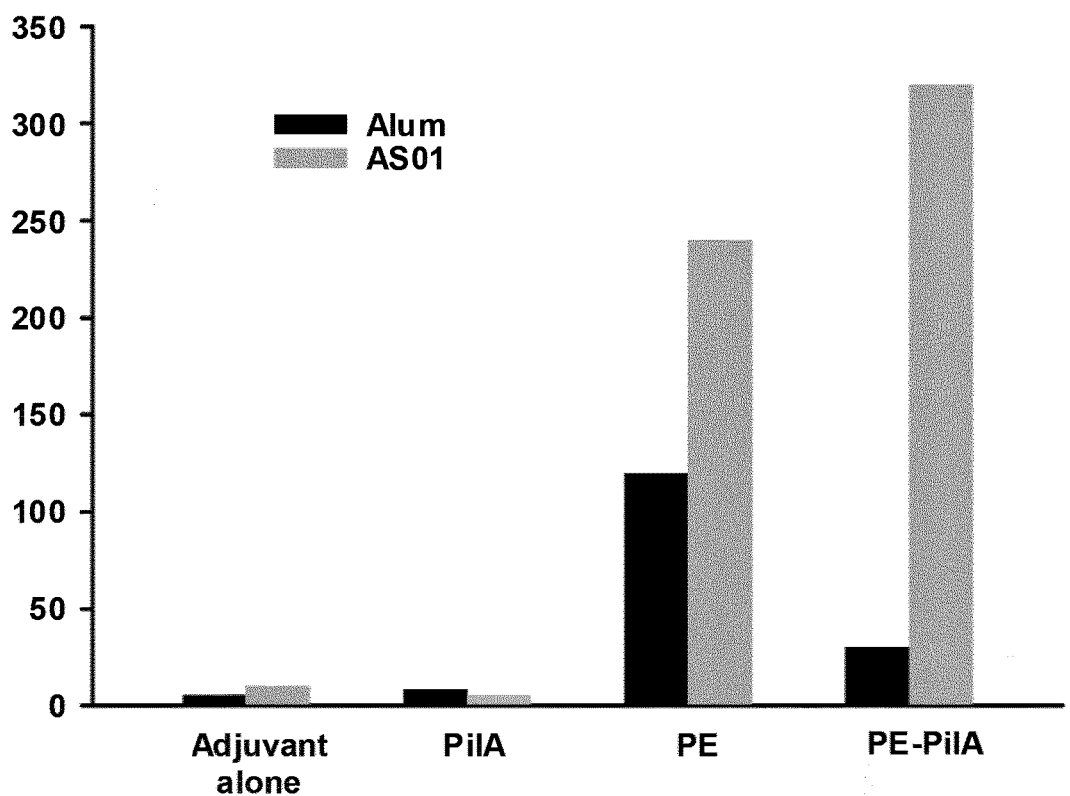

We aimed to determine whether antibodies from mice immunized with PE and PE-PilA were able to inhibit vitronectin binding to PE (FIG. 11). The sera used for the determination of the humoral responses were used for this experiment, without adjustment for antibody levels. As could be expected, sera from mice immunized with adjuvant alone or PilA alone (negative controls), even if anti-PilA antibodies were generated, were not able to inhibit the binding of vitronectin to PE. When immunized with PE-PilA admixed with alum, elicited antibodies could inhibit PE-vitronectin recognition, but to a lesser extent than after immunization with PE admixed with alum, reflecting the difference in anti-PE antibody levels between the two groups. When adjuvanted with AS01, PE and PE-PilA gave comparable anti-PE antibody levels after immunization and, accordingly, the levels of vitronectin binding inhibition were similar for the two groups.

Protection in the Nasopharyngeal Colonization Model

To assess the protective activity of the antigens against naso-pharyngeal colonization, we used a non-inflammatory nasopharyngeal colonization murine model. In this model, the bacteria colonize locally and do not spread to lungs, due to the small volume of inoculum, and do not infect systemically. Mice were immunized intranasally with adjuvant only (LT), PE alone, PilA alone or PE-PilA, all adjuvanted, before they were challenged via the same route with the 3224A or the 3219C NTHi strain. The intranasal route was used, as pilot experiments in our laboratories showed no protection with the parenteral route in this model.

Figure 12:
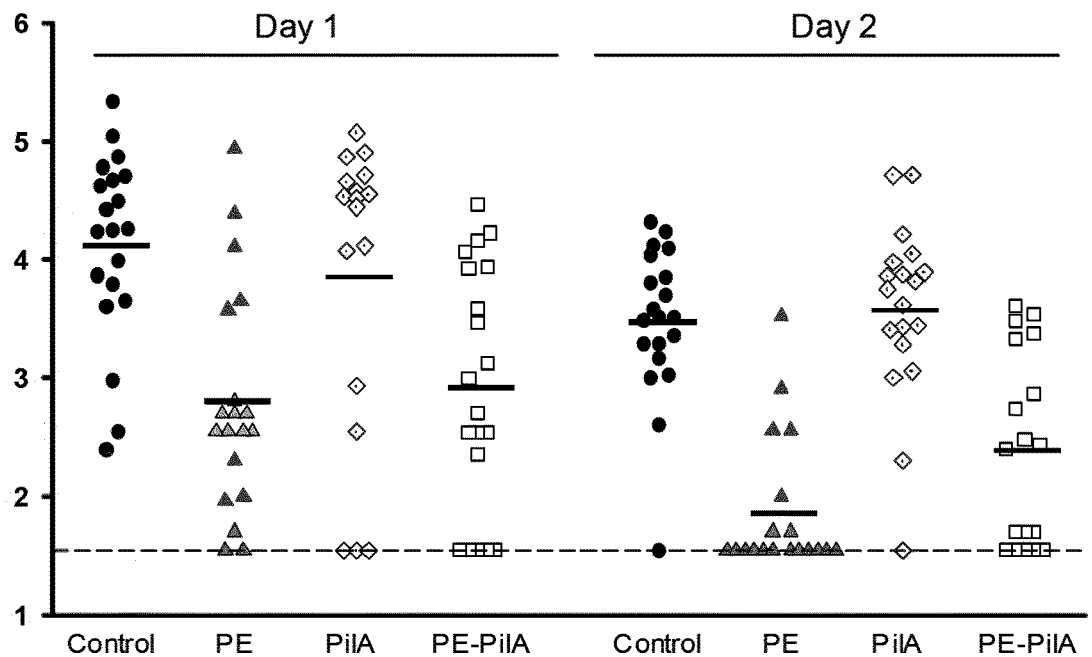

When cohorts were compared to each other over time, a significant reduction in the number of bacteria (p<0.001) was shown in the groups immunized with PE-PilA and PE (FIG. 12). No protection was observed with PilA alone (p=0.9937), which is in line with earlier observation showing that PilA alone is weakly or non-immunogenic in mice (FIG. 10).

The invention claimed is:

1. An engineered bacteriophage capable of binding to a commensal bacterium and inserting its genome polynucleotide into the commensal bacterium, but incapable of producing progeny, incapable of carrying out a lysogenic cycle and incapable of carrying out a lytic cycle within the commensal bacterium, wherein the engineered bacteriophage comprises a genome polynucleotide including at least one gene encoding at least one heterologous antigen(s) under the control of a promoter and the genome polynucleotide is engineered to delete all genes encoding lytic machinery proteins.

2. The engineered bacteriophage of claim 1 wherein the commensal bacterium is a part of skin, genital, oral or gut microbiome.

3. The engineered bacteriophage of claim 2 wherein the commensal bacterium is *Propionibacterium acnes, Staphylococcus epidermidis, Lactobacillus, Streptococcus gordonii* or *Escherichia coli*.

4. The engineered bacteriophage of claim 3 wherein the commensal bacterium is a *E. coli* bacterium and is part of the gut microbiome.

5. The engineered bacteriophage of claim 3 wherein the commensal bacterium is *S. epidermidis* or *P. acnes* and is part of the skin microbiome.

6. The engineered bacteriophage of claim 3 wherein the commensal bacterium is *Lactobacillus* and is part of the genital microbiome.

7. The engineered bacteriophage of claim 3 wherein the commensal bacterium is *Streptococcus gordonii* and is part of the oral microbiome.

8. The engineered bacteriophage of claim 1 wherein the genome polynucleotide is engineered to remove at least one gene encoding a capsid protein.

9. The engineered bacteriophage of claim 1 wherein the genome polynucleotide is engineered to delete at least one gene encoding a lysogeny machinery protein.

10. The engineered bacteriophage of claim 1 wherein the genome polynucleotide retains the origin of replication.

11. The engineered bacteriophage of claim 1 wherein the genome polynucleotide retains a phage origin of replication.

12. The engineered bacteriophage of claim 1 wherein the genome polynucleotide contains a bacterial origin of replication.

13. An engineered bacteriophage genome polynucleotide comprising a heterologous antigen gene encoding a heterologous antigen under the control of a promoter wherein the engineered bacteriophage genome polynucleotide is engineered to delete at least one gene encoding a capsid protein, and all genes encoding lytic machinery proteins, and optionally at least one gene encoding a lysogeny machinery protein, wherein when the engineered bacteriophage genome polynucleotide is packaged into a bacteriophage, the resulting bacteriophage is capable of binding to a commensal bacterium and inserting the engineered bacteriophage genome polynucleotide into the commensal bacterium, but is incapable of producing progeny, incapable of carrying out a lysogenic cycle and incapable of carrying out the lytic cycle within a commensal bacterium.

14. A pharmaceutical composition comprising the engineered bacteriophage claim 1.

15. An engineered bacteriophage according to claim 1 for use in the prophylactic prevention of disease, optionally infectious disease or cancer.

16. A pharmaceutical composition comprising the engineered bacteriophage genome polynucleotide of claim 13.

17. An engineered bacteriophage genomic polynucleotide according to claim 13 for use in the prophylactic prevention of disease, optionally infectious disease or cancer.

* * * * *